United States Patent
Jacobson et al.

(10) Patent No.: US 8,083,915 B2
(45) Date of Patent: Dec. 27, 2011

(54) METHODS FOR FORMING SMALL-VOLUME ELECTRICAL CONTACTS AND MATERIAL MANIPULATIONS WITH FLUID MICROCHANNELS

(75) Inventors: Stephen C. Jacobson, Knoxville, TN (US); J. Michael Ramsey, Knoxville, TN (US); Christopher T. Culbertson, Oak Ridge, TN (US); William B. Whitten, Lancing, TN (US); Robert S. Foote, Oak Ridge, TN (US)

(73) Assignee: UT-Battelle, LLC, Oak Ridge TN ( * ) Notice: Subject to any disclaimer, the term of this patent is extended or adjusted under 35 U.S.C. 154(b) by 758 days.

(21) Appl. No.: 11/875,031

(22) Filed: Oct. 19, 2007

(65) Prior Publication Data
US 2009/0032399 A1 Feb. 5, 2009

Related U.S. Application Data

(60) Continuation of application No. 10/668,930, filed on Sep. 23, 2003, now Pat. No. 7,297,243, which is a division of application No. 09/244,914, filed on Feb. 4, 1999, now Pat. No. 6,685,809.

(51) Int. Cl.
*G01N 27/447* (2006.01)
*G01N 27/453* (2006.01)
(52) U.S. Cl. .................................. 204/451; 204/601
(58) Field of Classification Search .......... 204/451–455, 204/601–605; 422/99, 100, 502, 503
See application file for complete search history.

(56) References Cited

U.S. PATENT DOCUMENTS

| 4,908,112 A | 3/1990 | Pace |
| RE34,757 E | 10/1994 | Smith et al. |
| 5,376,252 A | 12/1994 | Ekstrom et al. |
| 5,480,614 A | 1/1996 | Kamahori |

(Continued)

FOREIGN PATENT DOCUMENTS
EP 620432 10/1994

OTHER PUBLICATIONS

Ineos Nova Technical Bulletin PS303-1008 "Polystyrene Moisture Vapor and Gas Transmission Rates" downloaded from the www.ineos-nova.com site on Aug. 15, 2010.*
Dupont data sheet for Mylar® downloaded from the usa.dupont-tejinfilms.com site on Aug. 15, 2010.*

(Continued)

*Primary Examiner* — Alex Noguerola
(74) *Attorney, Agent, or Firm* — Dann, Dorfman, Herrell and Skillman, P.C.

(57) ABSTRACT

A microfabricated device employing a bridging membrane and methods for electrokinetic transport of a liquid phase biological or chemical material using the same are described. The bridging membrane is deployed in or adjacent to a microchannel and permits either ionic current flow or the transport of gas species, while inhibiting the bulk flow of material. The use of bridging membranes in accordance with this invention is applicable to a variety of processes, including electrokinetically induced pressure flow in a region of a microchannel that is not influenced by an electric field, sample concentration enhancement and injection, as well as improving the analysis of materials where it is desired to eliminate electrophoretic bias. Other applications of the bridging membranes according to this invention include the separation of species from a sample material, valving of fluids in a microchannel network, mixing of different materials in a microchannel, and the pumping of fluids.

13 Claims, 17 Drawing Sheets

U.S. PATENT DOCUMENTS

| | | | |
|---|---|---|---|
| 5,498,392 | A | 3/1996 | Wilding et al. |
| 5,630,924 | A | 5/1997 | Fuchs et al. |
| 5,705,813 | A | 1/1998 | Apffel et al. |
| 5,733,442 | A | 3/1998 | Shukla |
| 5,750,015 | A * | 5/1998 | Soane et al. .......... 204/454 |
| 5,842,787 | A * | 12/1998 | Kopf-Sill et al. .......... 366/340 |
| 5,872,010 | A | 2/1999 | Karger et al. |
| 5,882,496 | A | 3/1999 | Northrup et al. |
| 5,888,390 | A | 3/1999 | Craig |
| 5,942,443 | A | 8/1999 | Parce et al. |
| 5,976,336 | A | 11/1999 | Dubrow et al. |
| 6,012,902 | A | 1/2000 | Parce |
| 6,074,542 | A | 6/2000 | Dolnik et al. |
| 6,110,343 | A | 8/2000 | Ramsey |
| 6,136,272 | A | 10/2000 | Weigl et al. |

OTHER PUBLICATIONS

Robinson Rubber Products Company, Inc. EPDM or Ethylene Propylene entry in the Rubber Material Selection Guide downloaded from the www.robinsonrubber.com site on Aug. 15, 2010.*

Effenhauser et al., "Integrated Capillary Electrophoresis on Flexible Silicone Microdevices: Analysis of DNA Restriction Fragments and Detection of Single DNA Molecules on Microchips," Anal. Chem. Sep. 1, 1997, 69, 3451-3457.*

CL. Rice et al., "Electrokinetic Flow in a Narrow Cylindrical Capillary", The Journal of Physical Chemistry, vol. 69, No. 11, Nov. 1965.

D.C. Duffey et al., "Rapid Prototyping of Microfluidic Systems in Poly(dimethylsiloxane)", Analytical Chemistry, vol. 70, No. 23, Dec. 1, 1998.

CAPLUS abstract of Opdycke et al. ("Development and analytical performance of tubular polymer membrane electrode-based carbon dioxide catheters", Anal. Chem. (1986), 58(4), 950-6).

CAPLUS abstract of Gul et al., "Preservation of fruit and vegetable products in a controlled gas atmosphere using selectively-permeable film materials", Khranenie Plodoovoshchn. Prod. Kartofelya (1983), 265-71. ED. Sokol.

CAPLUS abstract of Hayano (JP 52120288 A2), Oct. 8, 1977.

JPO machine translation of Yoshitoshi et al. (JP 10-010088 A), Jan. 16, 1998.

* cited by examiner intersection fill rinse

Two-Stroke Microfluidic Vacuum Pump end of exhaust stroke exhaust stroke start on intake stroke start of exhaust stroke end of intake stroke

US 8,083,915 B2

METHODS FOR FORMING SMALL-VOLUME ELECTRICAL CONTACTS AND MATERIAL MANIPULATIONS WITH FLUID MICROCHANNELS

This application is a continuation of U.S. application Ser. No. 10/668,930 filed Sep. 23, 2003, now U.S. Pat. No. 7,297,243, which is a division of U.S. application Ser. No. 09/244,914, filed Feb. 4, 1999, now U.S. Pat. No. 6,685,809.

This invention was made with government support under contract DE-AC05-96OR22464 awarded by the U.S. Department of Energy to Lockheed Martin Energy Research Corp. and the government has certain rights in this invention.

FIELD OF THE INVENTION

This invention relates to microchip designs for the electrokinetic manipulation of fluidic chemical and biological materials. More specifically, this invention provides a microchip device which utilizes electrokinetic forces for the transport of materials through microchannels. The microchip device of this invention includes a membrane between adjacent or intersecting microchannels for passing ionic current while inhibiting bulk fluid flow.

BACKGROUND OF THE INVENTION

In order to facilitate the development of the biological and chemical sciences, microchip technologies are increasingly utilized to perform traditional chemical laboratory functions within a controlled microfabricated environment. These "on-chip" laboratories facilitate the precise transport and analysis of fluidic chemical and biological materials. Specifically, the decreased dimensions of the microchip devices provide integration of electronic and chemical processing technology while simultaneously yielding increased speed in analysis, reduction in reagent and/or sample consumption, and improved control in the automation of material manipulations.

Microfabricated devices that integrate chemical reactions with rapid analysis time have significant applications for high-throughput drug screening, automated analysis, and clinical chemistry. Microchips are characterized by reduced analysis time and reagent consumption, ease of automation, and valveless fluid control of sub-nanoliter volumes. A variety of electrically driven separations have been performed within microchannel networks. Microchips have also been developed for controlling chemical reactions, including arrays for solid-phase chemistry, reaction wells for polymerase chain reactions, channels with immobilized enzymes for flow injection analysis, and manifolds for homogenous enzyme assays. A microfluidic device using electrokinetic mixing of the organic solvents and reagents for the formation of an azo dye has been demonstrated.

The ability to design and machine channel manifolds with low-volume connections renders microchips suitable for combining several steps of an analytical process on one device. Microchips that combine chemical reactions with the speed and scale of CE analysis have been demonstrated for pre- and post-separation reactions, for DNA restriction digests with fragment sizing, and for cell lysis, multiplex PCR amplification and electrophoretic sizing.

Presently, chemical and biological materials are transported on microchips by way of electrokinetic techniques or an external pumping apparatus. The use of an external pumping apparatus is disfavored, however, because it demands additional hardware that is bulky and difficult to interface with the microchips. On the other hand, electrokinetic techniques, i.e., electroosmotically induced fluid flow or electrophoretic migration of ions, are the preferred methods of manipulating biological and chemical materials on microchip devices.

Electroosmosis is the bulk flow of fluid due to the combined effects of an electrical double layer in the presence of an axial electrical field. See, e.g., C. L. Rice and R. Whitehead, "Electrokinetic Flow in a Narrow Cylindrical Capillary", J. of Phys. Chem. (1965). The high density of ions in the diffuse region of the double layer are pulled electrostatically by the electric field along the walls of the channel. The layer of ions acts like a sleeve that is being pulled along the wall which adds momentum to the fluid by viscous drag. Under steady state conditions, which are reached in a microsecond timescale for the dimensions discussed herein, all fluid which is farther from the wall than the diffuse region are traveling at the same velocity. For example, water at pH 8 in a glass microchannel would travel at a velocity of $\simeq 1$ cm/s with an electric field strength of $\simeq 1$ kV/cm. Electrophoresis is the velocity imparted to an ion in solution when exposed to an electric field. The velocity of the ion is determined by the charge of the ion, the electric field strength, the viscosity of the solvent and the hydrodynamic radius of the ion. The direction of the ion movement depends on the direction of the electric field vector and the polarity of the charge on the ion. Electrophoresis necessarily only transports charged species. Electroosmosis imparts a velocity to all ions and neutral species. Under conditions where both electroosmosis and electrophoresis are operative, the net velocity of an ion will be the vector sum of the electroosmotic and electrophoretic velocities.

Electrokinetic transport mechanisms have been highly effective for demonstrating a number of highly useful experiments as identified above. A deficiency of presently demonstrated devices is the inability to make electrical contacts directly within microchannels. Efforts have been made to make such electrical contacts using a metal film that is photolithographically deposited onto a glass substrate so as to make contact with the fluidic microchannels. Such electrodes produce electrolysis products, most notably, oxygen and hydrogen gas from water, in all cases except under very limited conditions. The formation of a gas bubble can quickly separate the fluid in a microchannel and produces a nonconducting region which hinders the electrokinetic transport mechanisms.

SUMMARY OF THE INVENTION

The present invention provides a microfabricated device for liquid phase chemical and biological analysis. The device includes a substrate microfabricated with a series of channels and reservoirs. In accordance with this invention at least two of the microfabricated channels either intersect or are in close proximity to each other but do not overlap. A bridging membrane is created in one of the intersecting channels or between the two adjacent channels. The bridging membrane permits ionic current flow or gas transport while inhibiting bulk fluid flow therethrough. Reservoirs are formed in fluidic communication with the etched channels and are electrically connected with a high voltage power source to provide an electrical potential for electrokinetically driving and/or injecting materials from the reservoirs into the channels.

An object of the present invention is to provide a microfabricated device for performing sample loading and injection procedures that minimize electrochemically generated products in the transported sample.

Another object of the present invention is to provide reagent processing of electrokinetically driven products in a microfabricated device having a region that is uninfluenced by an electric field.

A further object of the present invention is to provide a microfabricated device which enables the transport of fluidic chemical and biological materials by electroosmotic forces into a region uninfluenced by an electric field.

Another object of the present invention is to provide a microfabricated device capable of concentrating ionic species.

A further object of the present invention is to provide a microfabricated device for separating or purifying a sample material.

Another object of the present invention is to provide a microfabricated device to facilitate the removal of electrochemically generated gas species.

A still further object of the present invention is to provide a microfabricated device to generate positive or negative pressure to facilitate hydraulic transport of gases or liquids.

Another object of the present invention is to provide a microfabricated device to effect valving in microfluidic structures.

BRIEF DESCRIPTION OF THE DRAWINGS

The foregoing summary, and the following detailed description, will be better understood when read in conjunction with the attached drawings, in which.

DETAILED DESCRIPTION OF THE PREFERRED EMBODIMENTS

A microfabricated device in accordance with the present invention is described in connection with several embodiments of microchannel networks utilizing a bridging membrane that is operable to pass ionic current, but minimize bulk fluid flow or transport of larger molecules, e.g. DNA. The bridging membrane allows electrical connection to fluidic microchannels without the problems related to electrolysis. This capability enables a number of important fluidic manipulations to be realized on microfabricated structures designed for the analysis and synthesis of chemical and biochemical materials.

A device in accordance with the present invention is particularly useful in connection with the analysis or processing of materials which are affected by electrophoretic bias. For example, post electrophoretic separation derivatization of a sample with a reagent would benefit from the devices of the subject invention. Also, the microfabricated device of the present invention permits electrochemical detection schemes in which a detection cell needs to be isolated from the electric field that facilitates transport of the sample material.

A device according to this invention uses the electroosmotic phenomenon to drive fluids, but includes a bridging membrane to isolate electric fields generated in the channels of the microfabricated device. The bridging membrane permits ionic current or gas to pass but minimizes or restricts bulk fluid flow. In a first embodiment, the bridging membrane provides a connection between a first channel and a second channel carrying materials to be analyzed or processed. One application of this configuration involves using the bridging membrane in a fluidic microchip for facilitating DNA concentration enhancement.

A second embodiment includes a first channel which is filled with a polyacrylamide gel as the bridging membrane.

The gel is disposed in the first channel adjacent to the second or analysis channel of the microfabricated device.

A third embodiment utilizes the bridging membrane to facilitate sample loading and injection procedures such that electrochemically generated byproducts in the sample are minimized. A second application of a device according to this invention uses a bridging membrane for separating or purifying a sample material.

A fourth embodiment includes a channel with a thin film electrode and a bridging membrane which facilitate the removal of electrochemically generated gas species from the microfabricated channel.

Additional applications employ bridging membranes to pump liquids or gases through microchannels. A further application employs bridging membranes to effect valving in microfluidic structures. Still further applications of this invention utilize bridging membranes for generating elevated pressures in a microchannel or to effect mixing of materials in a microchannel.

Adjacent Channel Embodiment

Figure 1:
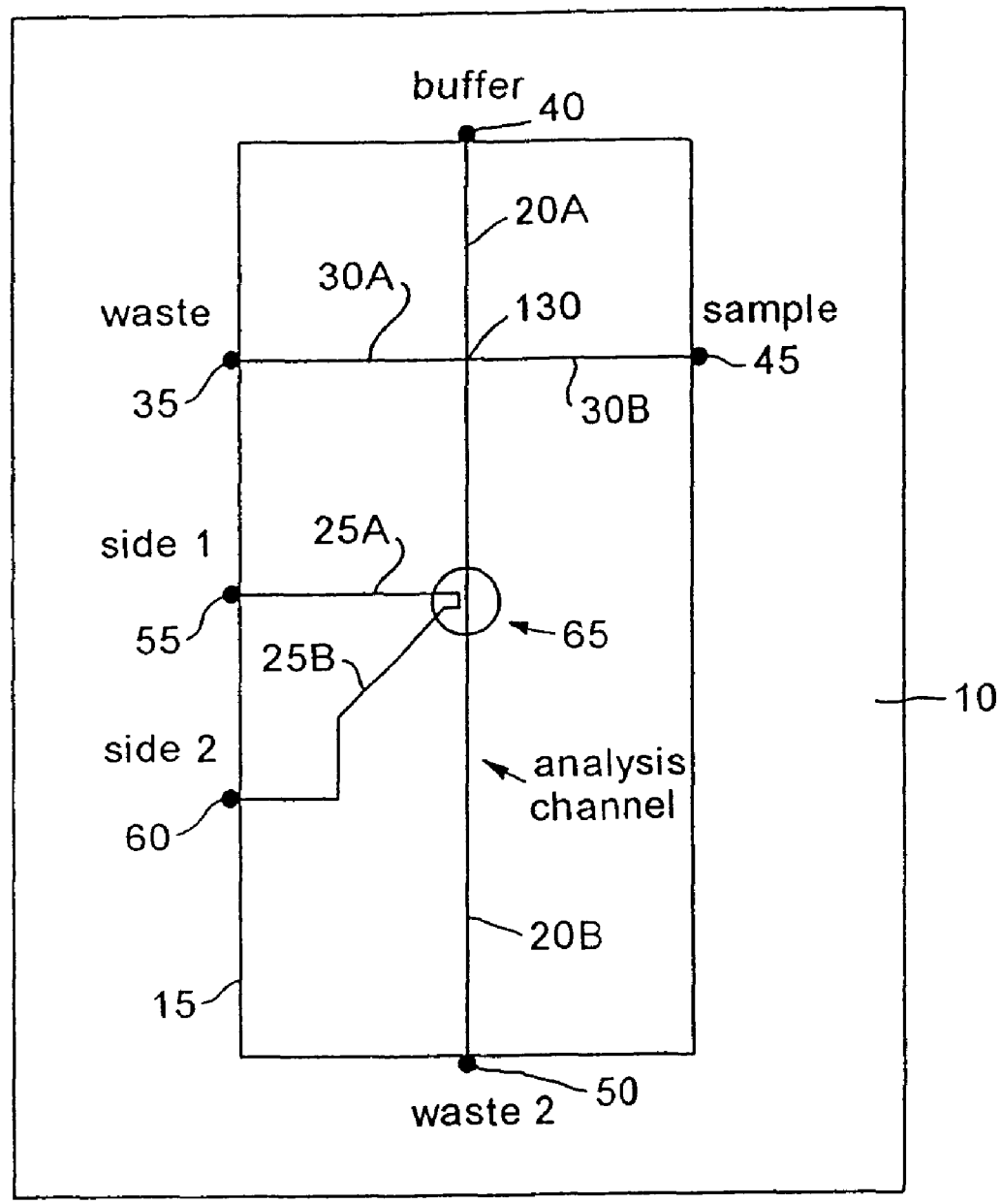
FIG. 1 is a schematic diagram of a fluidic microchip having a bridging membrane in accordance with the present invention.
Figure 1A:
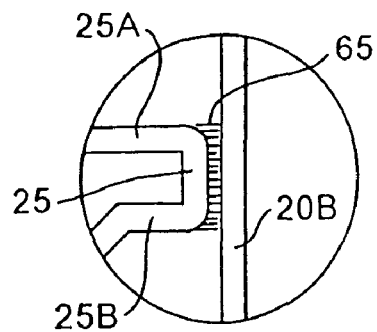
FIG. 1A is an enlarged view of the bridging membrane shown in FIG. 1.
Figure 1B:
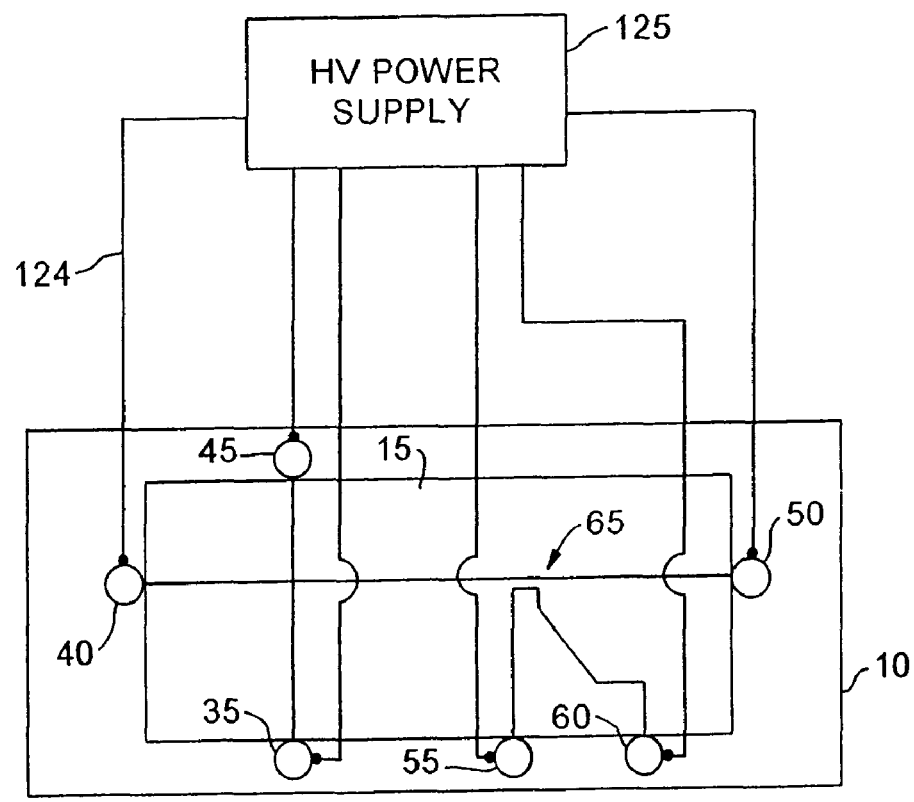
FIG. 1B is a schematic diagram showing the electrical connections to the microchip of FIG. 1.

Referring now to FIGS. 1, 1A, and 1B there is shown a microfabricated device labeled 5A in accordance with the present invention. Device 5A is fabricated from a solid substrate material 10. Glass is a preferred substrate material because it etches isotropically. However, silicon may be use instead because of the well developed technology permitting its precise and efficient fabrication. Also, other materials such as polymers, quartz, fused silica, sapphire, or plastics may be used. A series of microchannels 20A, 20B, 25, 25A, 25B, 30A, and 30B are formed in the top surface of the substrate 10 for facilitating the electroosmotic transport of biological and chemical materials. The microchannels 20A, 20B, 30A, and 30B intersect at a channel junction 130. Microchannel 25 interconnects side channels 25A and 25B adjacent to analysis microchannel 20B. A cover plate 15 appropriately affixed over the top surface of the substrate 10 seals the microfabricated surface of device 5A.

The microchip device 5A is fabricated using micromachining methods known to those skilled in the art. The micromachining methods available include film deposition processes such as spin coating and chemical vapor deposition, laser fabrication or photolithographic techniques such as UV or X-ray processes, or etching methods which may be performed by either wet chemical processes or plasma processes. Preferably, the microchannels 20A, 20B, 25, 25A, 25B, 30A, and 30B are formed on substrate 10 using a positive photoresist, photomask, and UV exposure. The channels are etched into the substrate 10 in a dilute, stirred HF/NH4F bath.

Cover plate 15 is bonded to the substrate 10 over the etched microchannels 20A, 20B, 25, 25A, 25B, 30A, and 30B by hydrolyzing the surfaces, spin-coating sodium silicate or potassium silicate onto the cover plate 15, bringing the substrate and cover plate into contact with each other, and then processing the assembly at temperatures typically ranging from about room temperature up to about 500° C. A suitable procedure is described in our copending application Ser. No. 08/645,497, the specification of which is incorporated herein by reference.

Microchip device 5A, includes a first waste reservoir 35, a buffer reservoir 40, a sample reservoir 45, a second waste reservoir 50, and first and second side reservoirs 55 and 60. The reservoirs are bonded to the substrate 10 over the terminal ends of micro-channels 30A, 20A, 30B, 20B, 25A, and 25B, respectively. The reservoirs of microchip device 5A are storage cells for liquid phase biological and chemical materials. The reservoirs supply materials for fluidic transport through the microfabricated channels.

As shown in FIG. 1B, a high voltage power supply 125 is connected to the reservoirs of device 5A to provide electric potentials thereto. A plurality of platinum wire electrodes 124 electrically connect the power supply 125 to the reservoirs of the microchip device 5A and contact the materials contained therein. The high voltage power supply 125 may be formed from a plurality of independent voltage sources or as a single voltage source and voltage divider network with a plurality of output terminals each providing a different voltage level. The electrokinetic driving forces are created by providing a potential difference between the various reservoirs in a controlled manner. Applied potentials on electrokinetically driven microchips are typically 1-3 kV, but can be higher or lower and the desired polarity depends on the experimental conditions.

Figure 2:
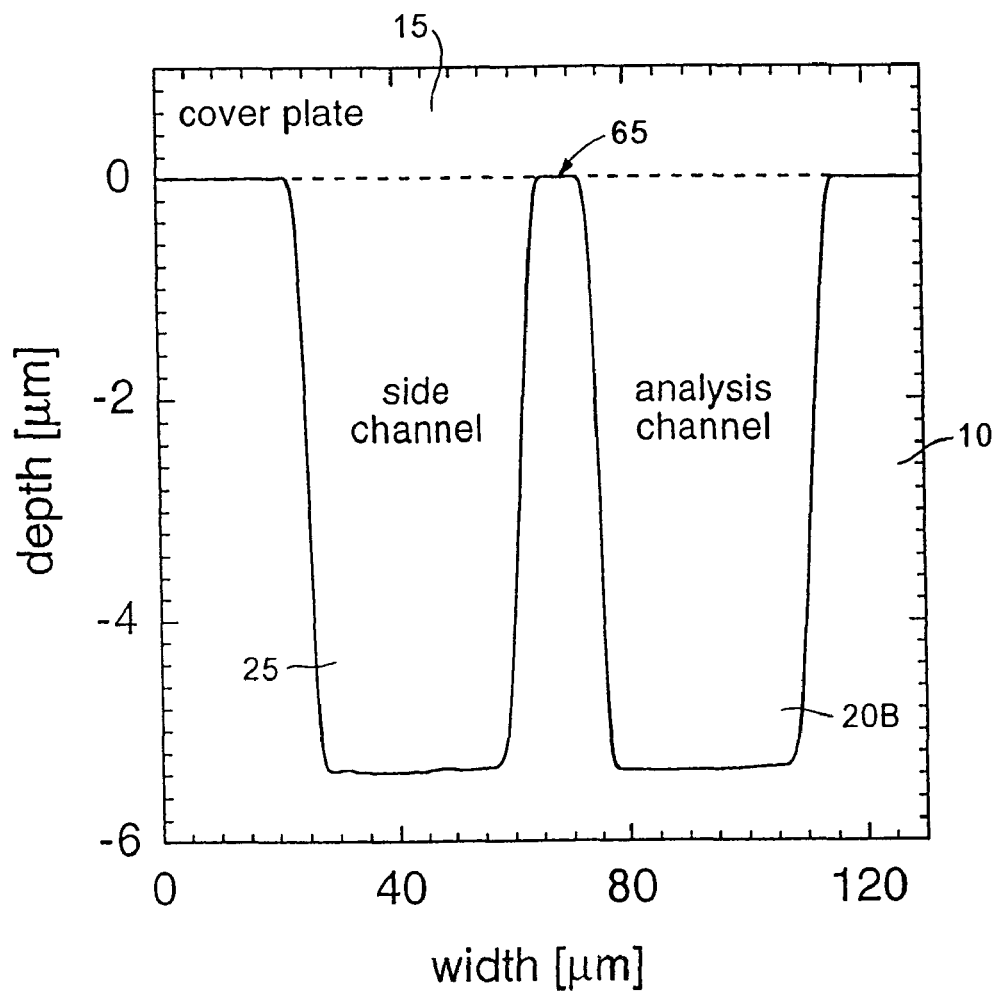
FIG. 2 is a graph showing a cross-sectional profile of two channels and a bridging membrane used in the microchip of FIG. 1.

Microchip device 5A as seen in FIG. 1A has a bridging membrane 65 (i.e., a thin electrically conductive porous glass layer) between microchannel 10b and channel 25. The microchip 5A has two channels in close proximity to each other. The distance between adjacent channels will vary depending on the etch time used to form the channels in the substrate, 0-35 µm bridges are typical. In the case of glass for example, the etch is isotropic so the longer the etch the closer the two channels come to physically connecting. Also, a low temperature bonding technique is used in order to generate a thin porous layer between the cover plate 15 and the substrate 10 at the bridging membrane junction 65. For microchip 5A, the preferred channel separation distance between channel 10b and channel 25 is about 6 µm. FIG. 2 shows a cross-sectional profile of an embodiment of channel 10b and 25, cover plate 15, and bridging membrane 65. The depth and width of the channels were determined with a stylus profilometer.

There are several potential alternative methods for forming a bridging membrane between two adjacent channels such as described for device 5A. The adjacent channels can be formed in sufficiently close proximity and the cover plate fixed to the substrate using a conventional high temperature bonding procedure. An electrical potential of sufficient strength can then be applied to the channels on opposite sides of the bridging membrane to thereby form electrical breakdown channels. Such breakdown channels provide a path for electrical conduction but have dimensions near that of the electrical double layer responsible for electroosmotic flow. Such channels are less efficient in producing electroosmotic flow and thus can act as bridging membranes. Another method of forming a bridging membrane is to directly fabricate the bridging channel(s) to have dimensions similar to the electrical double layer and thus allow electrical conduction without significant fluid conduction.

Working Examples

Figure 3A:
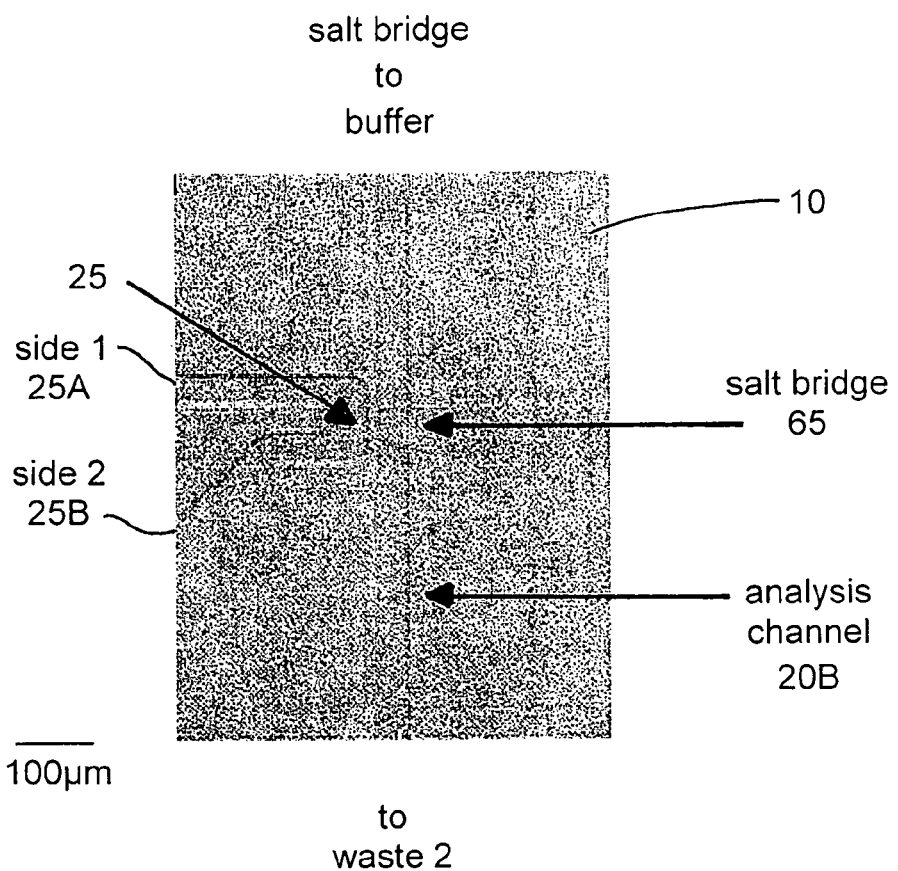
FIG. 3A is a white light image of the bridging membrane of FIG. 1 in accordance with the present invention.
Figure 3B:
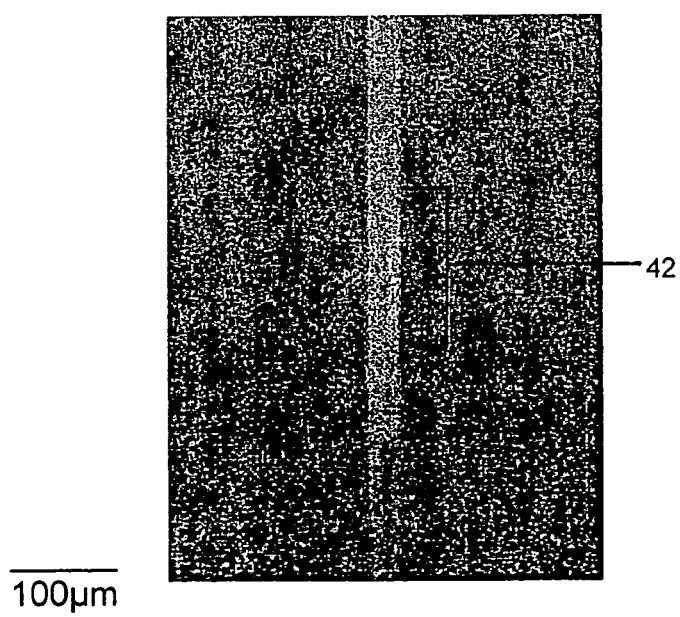
FIG. 3B is a fluorescence image of the rhodamine B buffer pumped beyond the bridging membrane connection of the microchip in FIG. 1.

Referring now to FIG. 3A, there is shown a portion of a physical embodiment of a microchannel device such as device 5A. The device shown utilizes a porous glass layer as the bridging membrane. The analysis channel 10b and the side channels 5a and 25B have been formed on the substrate 10. Operation of device 5A will now be described with reference to FIGS. 1 and 3B. A plug 42 of rhodamine B in a sodium tetraborate buffer is first loaded into analysis channel 10b using a fixed volume valve arrangement in which electric potentials of 0.6, 0.8, 0, and 0.6 kV are applied to the buffer reservoir 40, the sample reservoir 45, the first waste reservoir 35, and the first side reservoir 55, respectively. (0 kV corresponds to ground potential). Electric potentials of 1.0, 0.7, 0.7, and 0 kV are then applied to the buffer reservoir 40, sample reservoir 45, first waste reservoir 35, and first and second side reservoirs 55 and 60, respectively, to provide the electrokinetic driving force for transporting the plug 42 of rhodamine B into the analysis channel 20B. No voltage was applied to second waste reservoir 50, thereby allowing its potential to float. The plug of rhodamine B is transported in the analysis channel 20B by electroosmotic flow between the junction 130 and bridging membrane 65, and by electroosmotic pressure induced in the analysis channel 20B beyond the bridging membrane 65. A small fraction of the rhodamine B from plug 42 moves across the bridging membrane 65 to channel 25, but the bulk of the fluid material flows past the bridging membrane 65 as shown in FIG. 3B.

Figure 4:
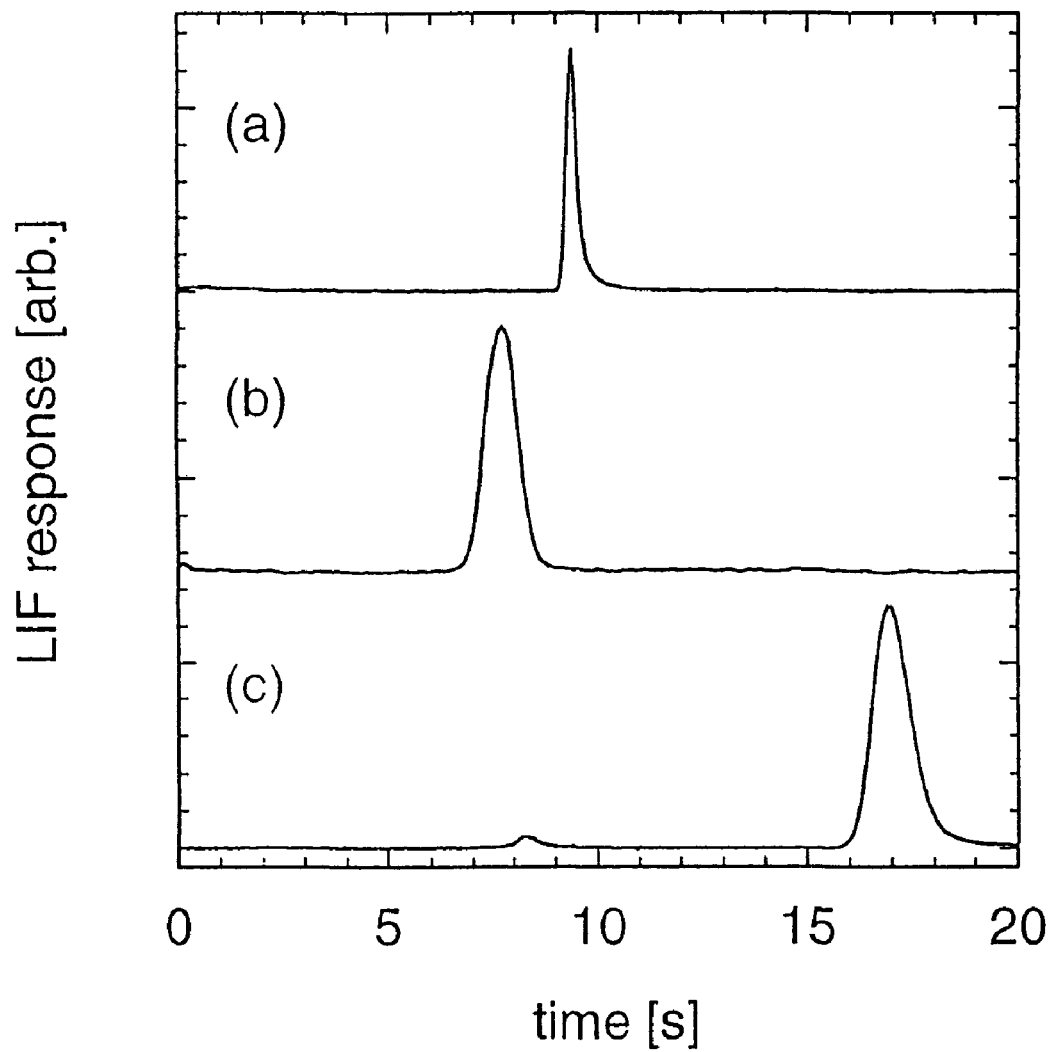
FIG. 4 is a graph of three profiles of a rhodamine B marker used to measure (a) electroosmotic flow without a bridging membrane, (b) electroosmotic flow using a bridging membrane, and (c) flow 10 mm beyond the junction using the bridging membrane.

The velocity of the sample plug 42 was measured using a single point detection scheme. Microchip 5A was first tested for electroosmotic flow under standard operating conditions, i.e., with no electric potential applied to the bridging membrane 65. The buffer reservoir 40, the sample reservoir 45, the first waste reservoir 35, and the second waste reservoir 50 were energized at voltages of 1.0, 0.7, 0.7, and 0 kV, respectively, to transport the sample plug along the analysis channel. No electric potential was applied to the other reservoirs. The measured electroosmotic velocity of the plug 42 in the vicinity of the bridging membrane was 1.07 mm/s. The rhodamine B concentration profile was monitored in the analysis channel 20B at a point adjacent to the bridging membrane 65. Graph (a) of FIG. 4 shows the timing of the sample as it passes the bridging membrane 65.

To measure the velocity with the side channels 25, 25A, and 25B engaged, i.e., with the bridging membrane in operation, electric potentials of 1.0, 0.7, 0.7, and 0 kV were applied to the buffer reservoir 40, sample reservoir 45, first waste reservoir 35, and first side reservoir 55, respectively. No electric potential was applied to the second waste reservoir 50 or the second side reservoir 60. The electroosmotic velocity measured in the vicinity of the bridging membrane was 1.29 mm/s. The profile was again monitored at the bridging membrane junction 65. Graph (b) of FIG. 4 shows the timing of the sample as it passes the bridging membrane 65. Graph (c) shows the timing of the same sample as obtained 10 mm downstream from the bridging membrane in a region of the analysis channel 10b that is free of an electric field. The velocity of the rhodamine B in the analysis channel 10 mm beyond the junction was measured as 1.09 mm/s. The velocity difference corresponds to an estimated pressure generated in the analysis channel of about 0.10 bar from the use of the bridging membrane.

The pressures or vacuums that are generated using these concepts depend on the dimensions of the channels, the interfacial characteristics and the properties of the fluid. The equation below shows the pressure dependence on some of these parameters.

$$P = \frac{3\varepsilon_0 \varepsilon \zeta E L}{\pi d^2}$$

The parameter $\varepsilon_0$ is the permittivity of free space, $\varepsilon$ is the fluid dielectric constant, $\zeta$ is the zeta potential, E is the axial electric field strength, L is the channel length over which electrokinetic pumping is taking place, and d is the channel depth. Greater pressures can be generated by reducing the channel depth, but not without bounds. When the channel depth approaches the electrical double layer thickness, electroosmotic pumping becomes less efficient with corresponding reductions in the average fluid velocity produced for a given electrical field, as understood by those skilled in the art. The variation of fluid flow and effective pressure generation with varying channel depths and double layer thicknesses, at fixed electrical field strength or current, provides the ability to design structures that generate for different purposes as described in this application. Effective pressures that can be electrokinetically generated can be controlled with channel depth and length. In addition by making channel dimensions similar to the double layer thickness, fluid conduction can be inhibited while maintaining electrical current.

Figures 10A, 10B:
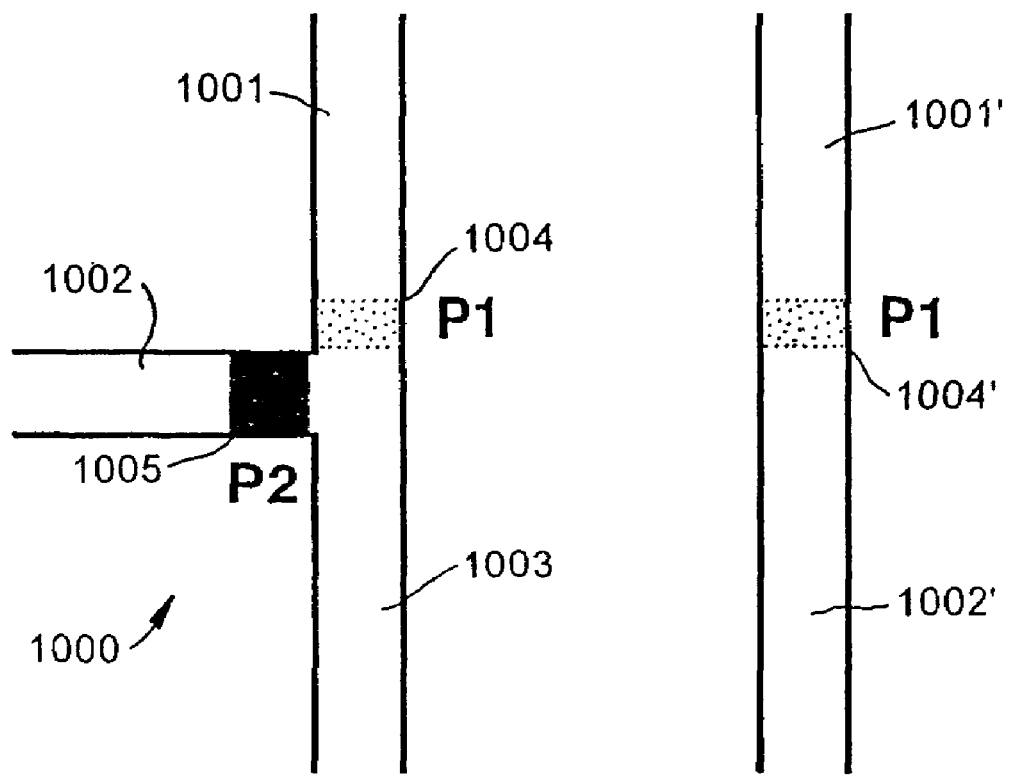
FIG. 10A is a schematic diagram of a "tee" microchannel network having a bridging membrane in two of the microchannels thereof.
FIG. 10B is a schematic diagram of a single, straight channel of a microchannel network having a bridging membrane disposed therein.

One way to effectively reduce the channel depth or pumping depth dimension is to form a porous network of channels such as formed by the silicate bonding methods used in the working examples described hereinabove. The pore size of the bridging membrane acts as the channel depth in the equation above for the pressure P, while the many separate paths through the membrane increase the flow rate of fluid. An example of such a device is shown in FIG. 10A. A tee microchannel network 1000 is formed with channel segments 1001, 1002, and 1003. A bridging membrane 1004 is formed in channel 1001 and a second bridging membrane 1005 is formed in channel 1002. The bridging membranes 1004 and 1005 are positioned near the intersection of the channels.

To generate pressure in channel 1003 a voltage is applied between the entrance to channel 1001 and the entrance to channel 1002 so as to transport fluid from channel 1001 to channel 1002. The pumping characteristics, i.e., the fluid flow rate at a given electric field strength, are different for the two membranes. Membrane 1004 is formed to provide a higher pumping rate than membrane 1005. Under such conditions and given zero flow rate out channel 1003, a pressure will be generated in channel 1003 corresponding to the pressure drop across membrane 1004. Such generated pressures could be used to push a mobile phase through channel 1003 that is packed with stationary support particles while providing an electric field free region in channel 1003. Adjusting the applied potential to reverse the direction of fluid transport will allow a vacuum to be created in channel 1003.

An alternative form of this arrangement is shown in FIG. 10B which includes an upper channel 1001' and a lower channel 1002'. The upper channel 1001' has a bridging membrane 1004' formed therein. When a voltage is applied between the entrances to channels 1001' and 1002' so as to move fluid from channel 1001' to channel 1002', a pressure is generated in the lower channel 1002' corresponding to the pressure drop characteristics of bridging membrane 1004'. However, this implementation results in an electric field being present in the lower channel 1002', the high pressure microchannel segment.

Figure 8:
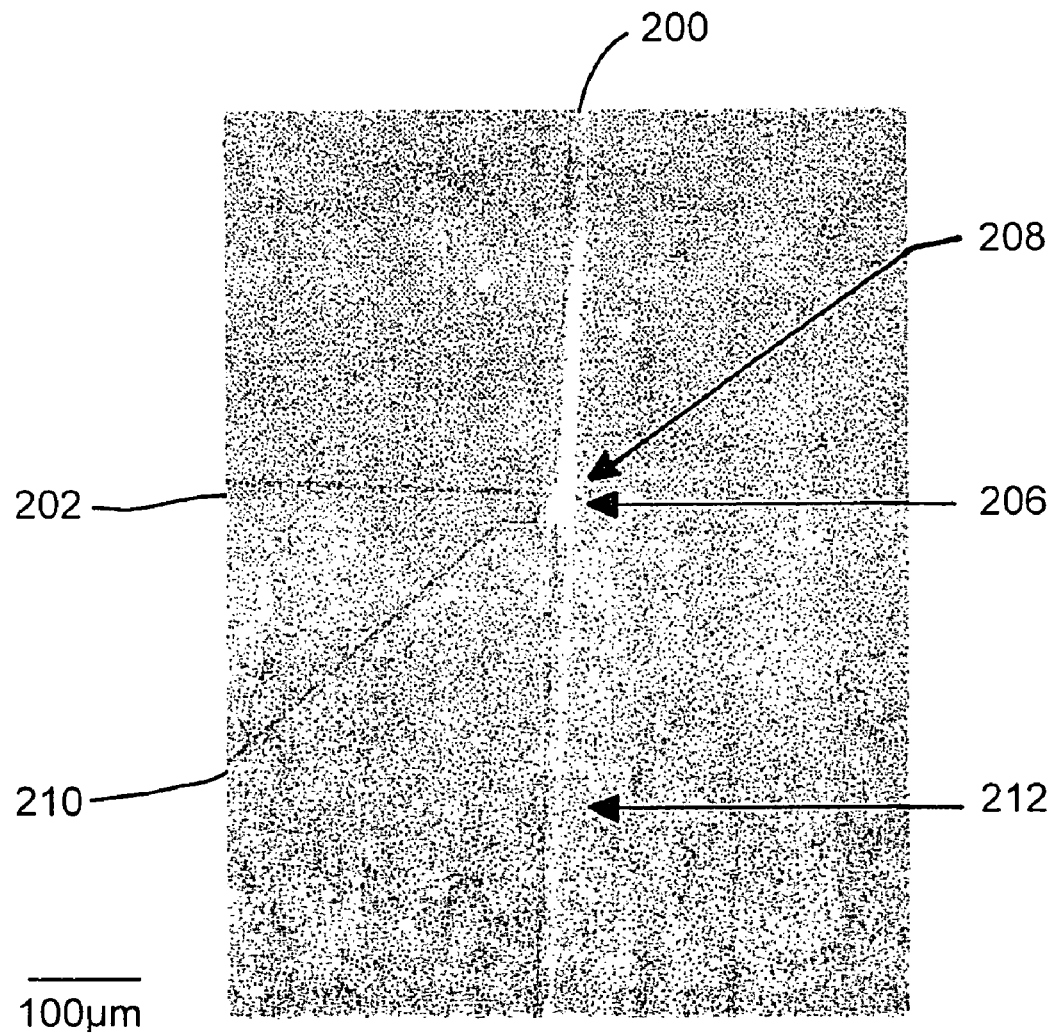
FIG. 8 is a backlit image of a further embodiment of a bridging membrane according to this invention.

Referring now to FIG. 8, there is shown a second working example embodied as microchip 5B in accordance with the present invention. The working example illustrates the use of microchip 5B for concentration enhancement of DNA using a bridging membrane incorporated into the microfluidic network formed on the chip. The microfabricated bridging membrane structure of microchip 5B is similar in design to microchip 5A shown in FIG. 1 and described previously herein. FIG. 8 is a backlit image of an actual microchip combined with a fluorescence image of the DNA material 208 concentrated in the analysis channel 212 at the bridging membrane 206 (bright spot at the bridging membrane). The concentration enhancement occurs when an electrical potential is applied between the sample channel 200 and the first side channel 202. No electrical potential is applied to the analysis channel 212 in this case, but an electric potential of the same polarity as applied to the sample channel 200, if applied to waste channel 212, would further assist in confining the spatial extent of the concentrated DNA sample 208 adjacent to the bridging membrane 206. The bridging membrane 206 allows small ions to pass but prevents the larger molecules of the DNA 208 from migrating through the bridging membrane 206 in the presence the electric field. The bridging membrane thus acts as a physical barrier through which the DNA molecules 208 cannot pass and, over time, the DNA 208 accumulates at the bridging membrane junction 206. The amount of DNA 208 collected at the bridging membrane 206 is related to the electric field strength, the time of accumulation, and the electrophoretic mobility of the DNA 208. In this example, the sample channel 200 is grounded, and 1 kV is applied to the second side channel 210. The accumulation time is approximately 1 minute. The analysis and side channels, 212 and 202 respectively, are coated with covalently linked linear polyacrylamide to minimize electroosmotic flow and are filled with 3% linear polyacrylamide, a common sieving medium for DNA separations.

Figure 9:
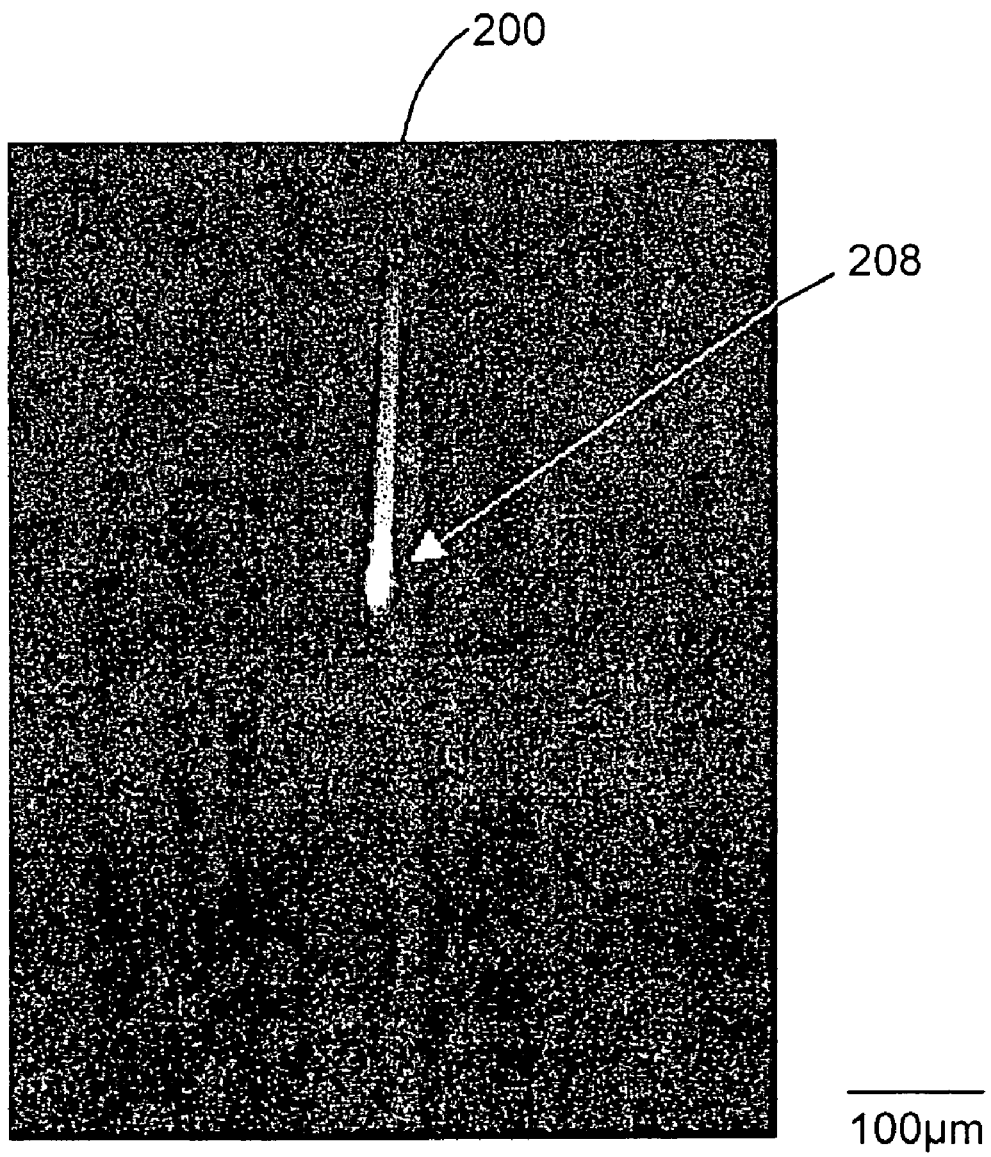
FIG. 9 is a fluorescence image of DNA concentration at the bridging membrane of FIG. 8.

FIG. 9 shows a fluorescence image of the double stranded DNA 208 (ΦX-174, Hae III digest) intercalated with a dye, TOPRO, and excited using an argon ion laser (514.5 nm) without backlighting of the bridging membrane connection 206. The bright spot at the center of the image is the DNA material 208 that has been transported from the sample reservoir 200 and concentrated at the bridging membrane 206. This technique can be used to concentrate either single or double stranded DNA. Clearly the intensity of the fluorescence is greater in the vicinity of the bridging membrane 206 than on the sample reservoir side of the analysis channel or in the analysis channel below the bridging membrane 206. Also, with the addition of a channel to the microchip design both a constant volume or variable volume valve can be implemented to inject a sample onto the analysis channel 212 following concentration enhancement at the bridging membrane. Such a DNA concentration enhancement tool would be valuable for DNA analysis when DNA concentrations would otherwise be too low to measure using standard techniques. It will be readily apparent to those skilled in the art that such as device is useful for other types of materials that are to be analyzed such as proteins and synthetic polymers.

Intersecting Channel Embodiments

Figures 5A, 5B:
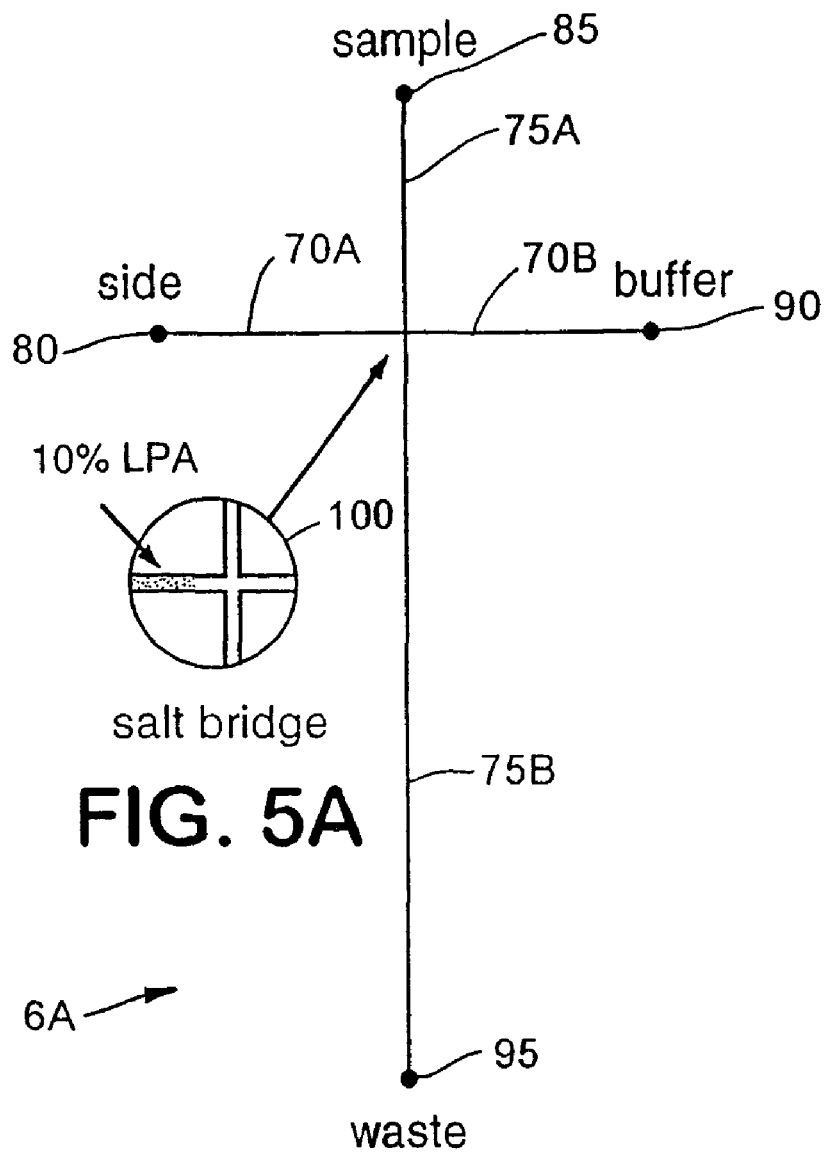
FIG. 5B is a schematic diagram of a second embodiment of a microchip in accordance with the present invention.
FIG. 5A is an enlarged view of the intersection of the side channel and analysis channels of FIG. 5B showing the location of the bridging membrane.

Referring now to FIG. 5, there is shown another embodiment of a microchip 6A in accordance with the present invention. Microchip 6A has side channel portions 70A and 70B and analysis channel portions 75A and 75B formed thereon. The side channel portions 70A, 70B intersect with analysis channel portions 75A, 75B of microchip 6A. In preparing microchip 6A, the cover plate was bonded to the substrate over the etched channels by hydrolyzing the facing surfaces, bringing them into contact with each other, and heating the assembly at 500° C. Microchip 6A includes a side reservoir 80, a sample reservoir 85, a buffer reservoir 90, and a waste reservoir 95. The reservoirs are affixed with epoxy to the substrate at the point where the channels extend beyond the cover plate. Electrical connection between the high voltage power supply and the reservoirs is made using platinum wire connection as illustrated for the embodiment of FIG. 1B. Side channel portion 70A is filled with 10% (w/v) acrylamide that is polymerized to gel form in situ. The polymer allows ionic current to pass, but inhibits bulk fluid flow in the manner discussed above. The polymer extends to within about 1 mm of the intersection. The three remaining channel portions, 70B, 75A, and 75B are filled with a buffer solution to prevent polymerization of the acrylamide in those channel portions.

Working Example

Figure 6A:
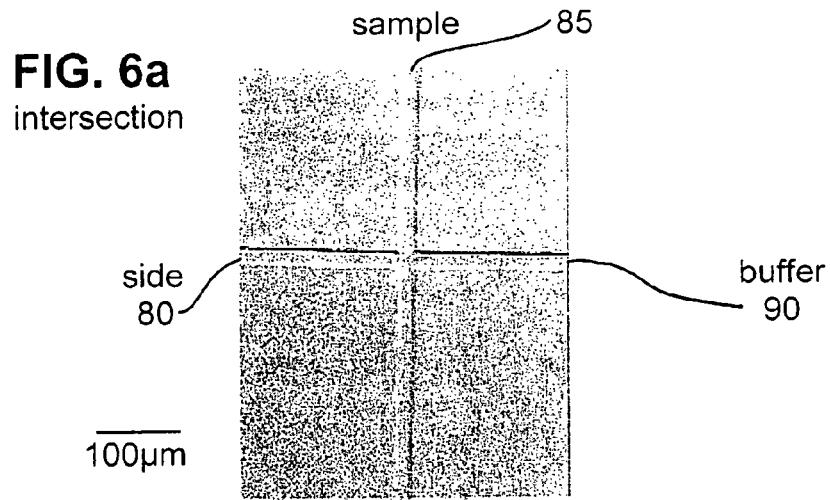
FIG. 6A is a white light image of the intersection portion of the fluid channels shown in FIG. 5B.
Figure 6B:
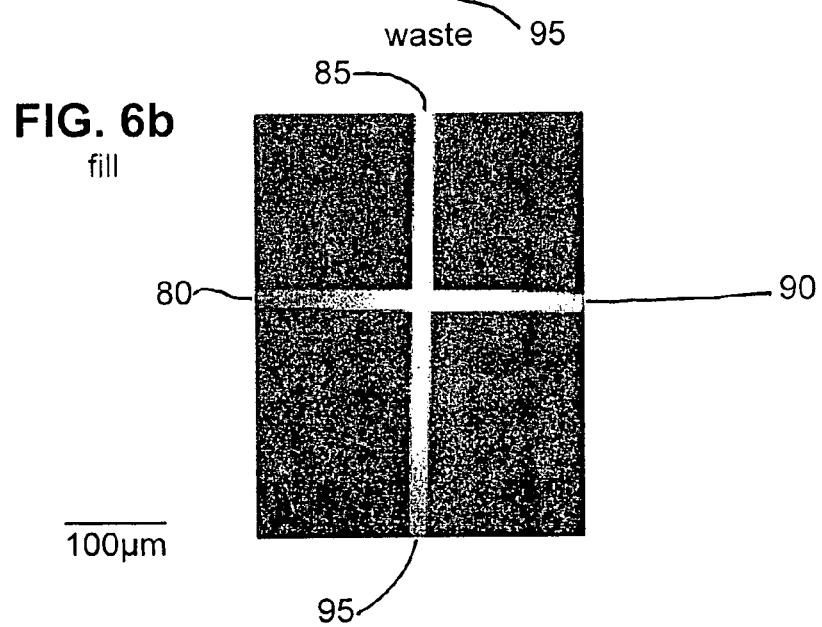
FIG. 6B is a fluorescence image showing the filling of the intersection portion of the fluid channels of FIG. 6A with rhodamine B buffer.
Figure 6C:
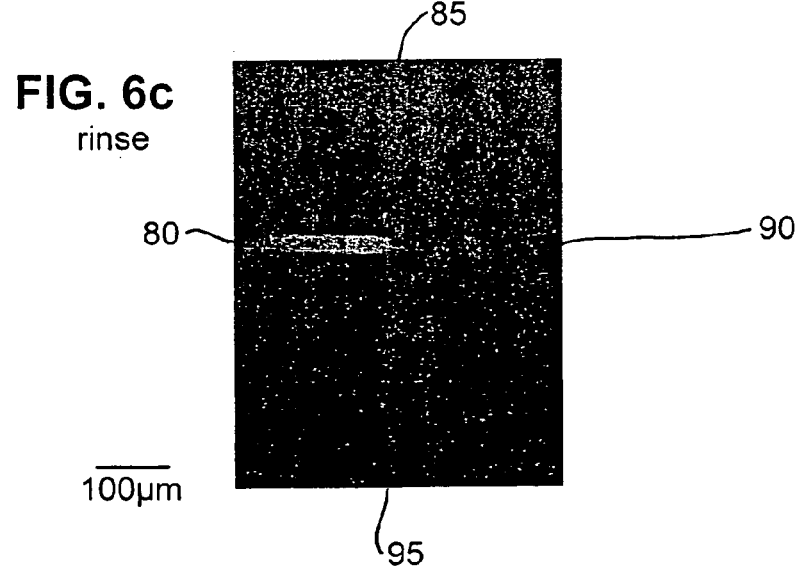
FIG. 6C is a fluorescence image showing the rinsing of the intersection of FIG. 6B with a buffer.

Referring now to FIG. 6A, there is shown an example of a microchip similar to that shown in FIG. 5. In FIG. 6A, the chip is backlit to show the microchannels and the intersection thereof. FIG. 6B, shows the intersection being filled with rhodamine B buffer by applying potentials of 1.0 kV and 0 kV to the sample reservoir 85 and side reservoir 80, respectively. Rhodamine B is pumped into the buffer channel 70B and waste channel 75B which are free of electric fields. In FIG. 6C the intersection is rinsed with a buffer solution by applying 1 kV, 0 kV, 0 kV, and 0 kV to the buffer reservoir 90, sample reservoir 85, side reservoir 80, and waste reservoir 95, respectively. A small amount of rhodamine B is left in the side channel due to a small dead volume. Because of the high electrical resistance of the polymer filled channel, the utilization of the applied electric potential for the electroosmotic pumping effect is not as efficient in this example as for the embodiments described previously herein. However, polymer plugs having a lower electrical resistance could be generated using plugs of different spatial extent or conductivity.

Additional Embodiments and Applications

Figure 7:
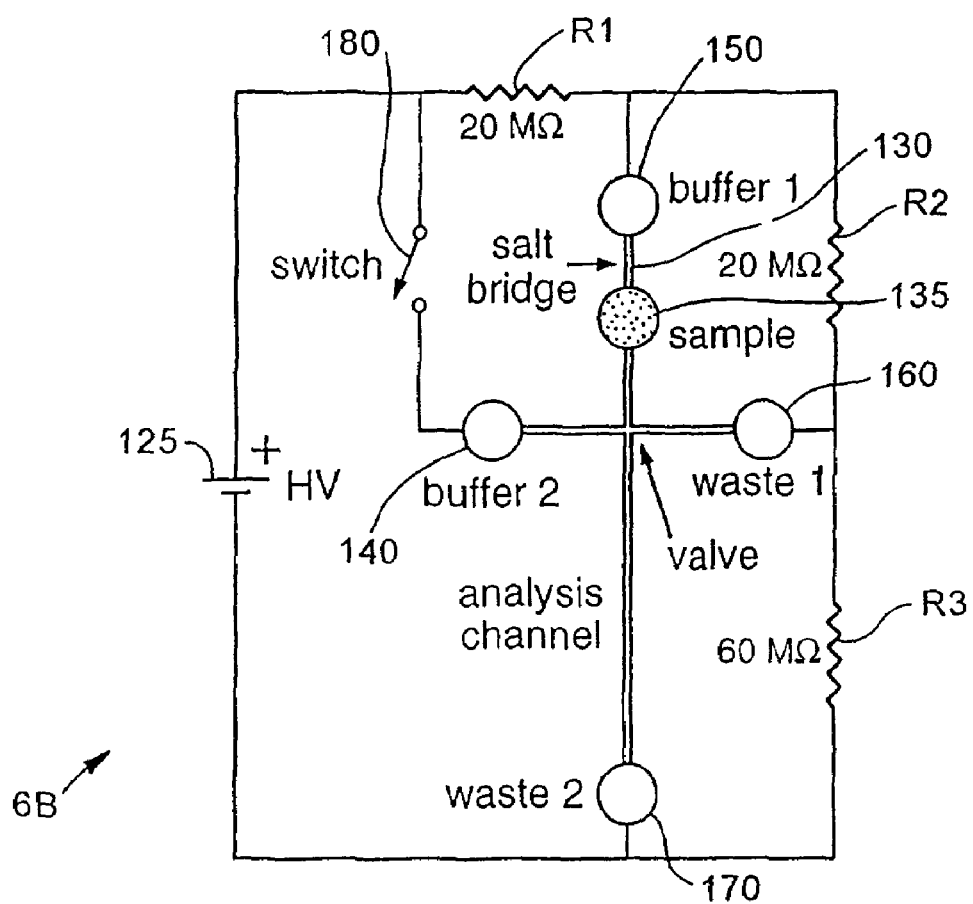
FIG. 7 is a schematic diagram of a further embodiment of a microchip according to this invention.

Referring now to FIG. 7, there is shown an arrangement for controlling sample loading and injection procedures which includes a microchip 6B according to the present invention. Microchip 6B includes a first buffer reservoir 150, a second buffer reservoir 140, a sample reservoir 135, a first waste reservoir 160, and a second waste reservoir 170. A high voltage source 125 is connected to the first buffer reservoir 150, the first waste reservoir 160, and the second waste reservoir 170 through a voltage dividing network consisting of resistors R1, R2, and R3. A switch 180 is connected between the high voltage source 125 and the second buffer reservoir 140. In the embodiment shown in FIG. 7, the high voltage source is not directly connected to the sample reservoir 135 as in the embodiment of FIG. 5. Instead, electrical connectivity is made through a small channel extending between the first buffer reservoir 150 and the sample reservoir 135. A bridging membrane 130 is formed in the microchannel between the first buffer reservoir 150 and the sample reservoir 135. The bridging membrane 130 is formed of a free solution or a polyacrylamide gel for the purpose of minimizing any electrochemically generated products in the sample material.

To perform injections, a variable volume valve is configured with 1.0 kV, 0.8 kV, 0.6 kV, and 0 kV applied to the second buffer reservoir 140, first buffer reservoir 150, first waste reservoir 160, and second waste reservoir 170. To inject a sample plug, the switch 180 is opened at the start of the injection period. This removes the electric potential at the second buffer reservoir 140 and continues to apply a potential to the first buffer reservoir 150, first waste reservoir 160, and second waste reservoir 170. At the end of the injection period, switch 180 is closed. The injection procedure of this embodiment is essentially identical to an embodiment where the high voltage is applied directly in the sample reservoir. However, it avoids to a large extent the problems associated with the electrochemical generation of undesired products in the sample material.

Figure 11:
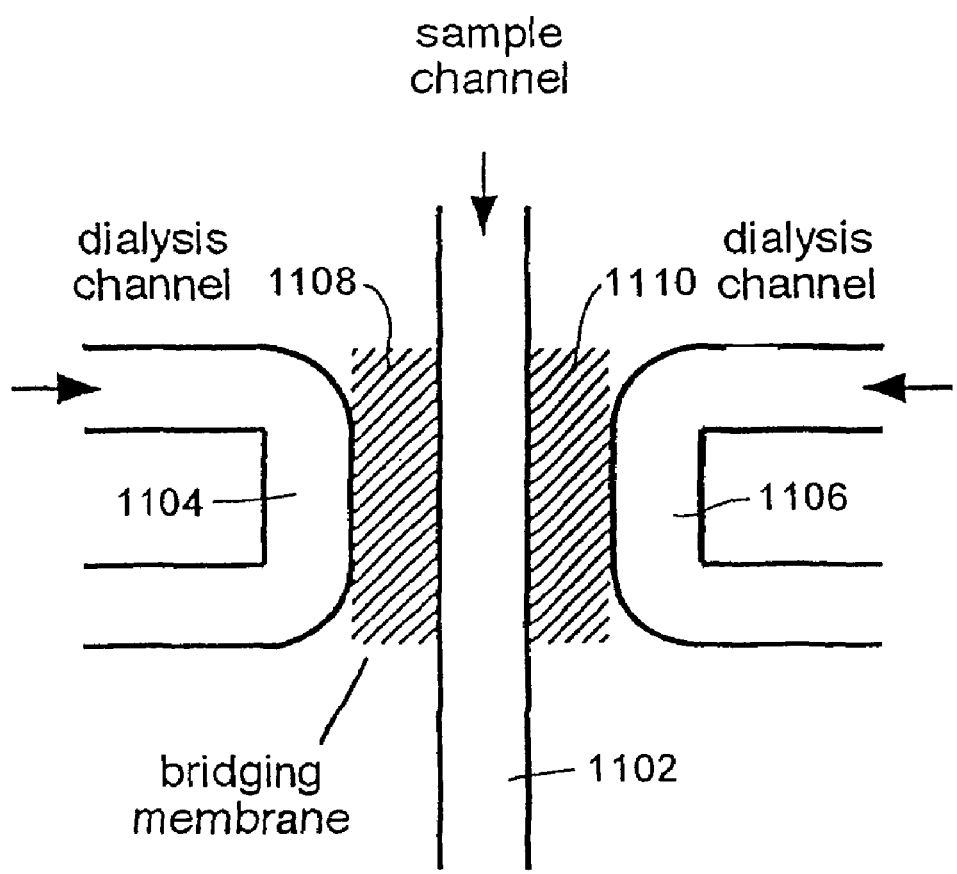
FIG. 11 is a schematic diagram of an arrangement of microchannels and bridging membranes in accordance with another aspect of this invention for accomplishing ionic or molecular separation of a fluidic material.

A second use of a bridging membrane according to the present invention is the separation of ions and/or molecules in a sample material based upon their properties such as charge, size, or a combination thereof. The microchip is fabricated with a sample channel and a dialysis or electrodialysis channel on one or both sides of the sample channel. A preferred embodiment of this application is shown schematically in FIG. 11. A sample channel 1102 is formed in fluid communication with a sample reservoir (not shown) and a waste reservoir (not shown). A first dialysis channel 1104 and a second dialysis channel 1106 are formed on opposite sides of the sample channel 1102. The dialysis channels 1104 and 1106 are separated from the sample channel 1102 by bridging membranes 1108 and 1110, respectively. A microchip embodiment of this arrangement is fabricated as described above with reference to the embodiment of FIG. 1. The sample material and dialysis buffer are transported through their respective channels using either electrokinetic transport or a hydraulic force. In addition, a potential difference can be applied between the sample and dialysis channels to cause or prevent the transport of ions through the bridging membranes 1108, 1110 from the sample channel 1102 to the dialysis channels 1104, 1106, respectively. In this manner, small ions or molecules are transported out of the sample channel for analysis or to remove them from the sample material in the sample channel 1102. Neutral small molecules can diffuse passively through the bridging membranes 1108, 1110 with or without an electric field present. Moreover, without a potential difference applied between the sample channel 1102 and the dialysis channels 1104, 1106, small ions diffuse passively across the bridging membrane. The efficiency of the dialysis process in this arrangement depends on dimensions of the sample channel, the dialysis channel(s), and the bridging membrane(s), the residence time of the sample material near the bridging membrane, and the magnitude of the electric potential applied between the sample and dialysis channels.

When an electrode material is in contact with water, reduction/oxidation reactions occur at the electrode surface producing hydrogen and/or oxygen gas. This gas evolution quickly leads to macroscopic gas bubble generation and can disrupt the current and electrokinetic flow especially in channels formed in glass or quartz substrates. In a further embodiment of a microchip according to this invention for generating pressure-driven flow by electroosmotic pumping a porous substrate is used with a metal film electrode. In this arrangement the bridging membrane conducts gas phase species rather than electrical current, but still inhibits bulk fluid transport. A working example of that arrangement was demonstrated using a polydimethylsiloxane (PDMS) substrate and a metal film for the ground electrode in one of the microfluidic channels. The PDMS acts as a bridging membrane that facilitates the removal of electrochemically generated gas phase species from the microfluidic channel because small gas phase molecules diffuse through the PDMS more rapidly than in glass. This greater diffusion allows chips formed with a PDMS substrate to be electrically contacted using a metal electrode at any point along a channel without the problem of macroscopic gas bubble formation in such a channel. Electrically contacting a microchip channel using this method enables the creation of an electric field-free region in the channel past the electrode, and materials can be pumped through this region using the pressure generated in the electroosmotic pumping region.

Figure 12:
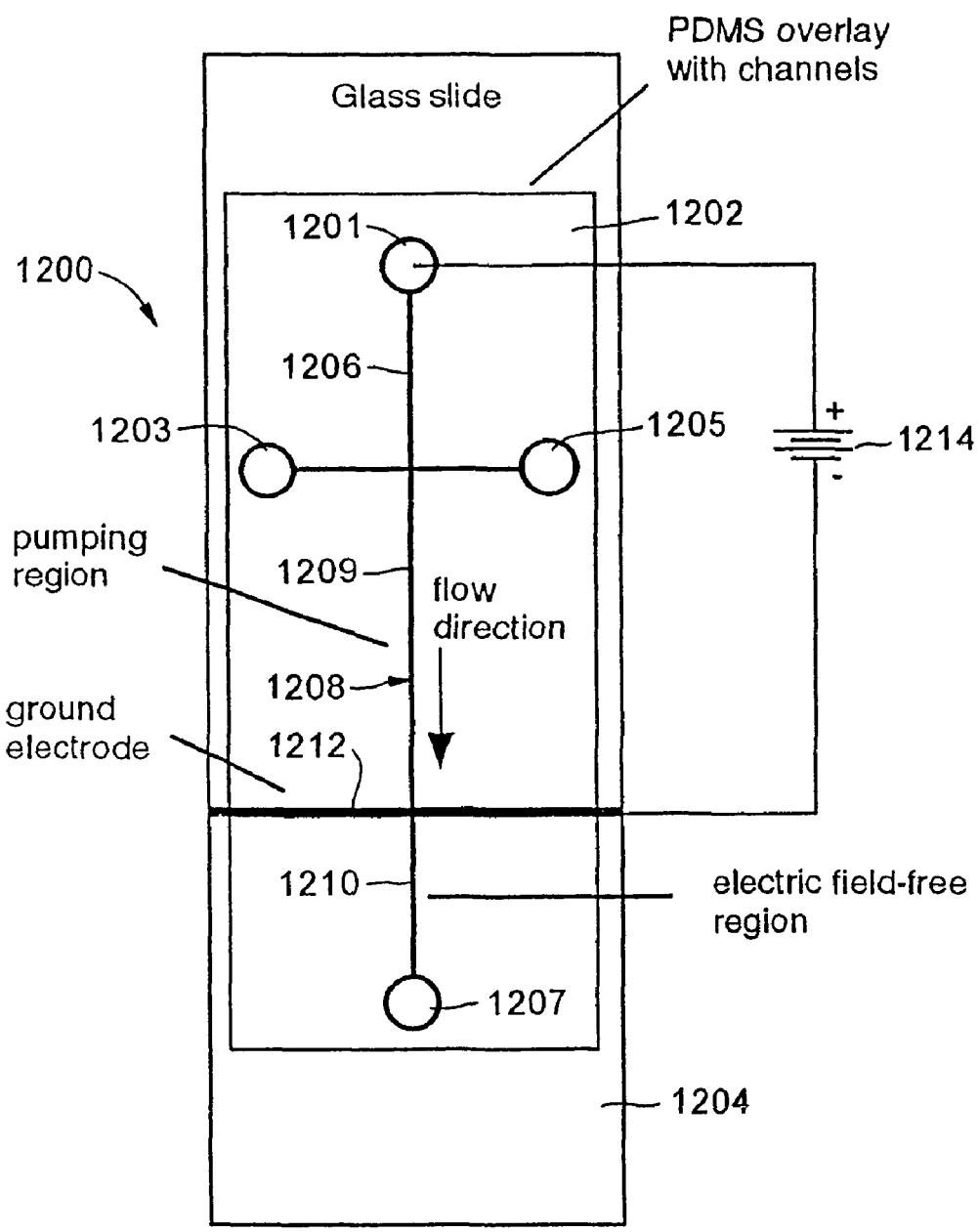
FIG. 12 is a schematic diagram of a microchip in accordance with a further aspect of this invention for effecting out removal of gas species generated in the fluidic materials when electrically energized.

To demonstrate this application, a hybrid microchip was fabricated using a PDMS substrate into which channels were molded and a glass cover plate on which metal electrodes were fabricated. The device 1200 is shown schematically in FIG. 12. The microchannel network includes a sample channel 1206, an analysis channel 1208, and a pair of side channels intersecting with the sample and analysis channels formed on a PDMS substrate 1202. To form the microchannel network on the PDMS substrate 1202, the PDMS material was polymerized in a negative silicon mold. The silicon mold was made by standard microfabrication techniques. Following polymerization, the PDMS substrate was removed from the silicon mold. A grounding electrode 1212 was formed by sputtering a chrome electrode pattern onto a glass substrate 1204. The glass substrate 1204 and the PDMS substrate 1202 were then oxidized and sealed together. The oxidation and sealing process used a plasma cleaner of a known type. Reservoirs 1201, 1203, 1205, and 1207 were formed in the PDMS substrate in fluid communication with the sample channel 1206, the analysis channel 1208, and the side channels, respectively.

Prior to use, the microchannels were rinsed with 1M NaOH and distilled water. This procedure was selected to minimize gas bubble formation when a large electric potential is used. Reservoir 1201 was filled with 1.0 µm diameter fluorescently labeled particles in a 20 mM SDS/10 mM HEPES buffer (pH 7.4). Reservoirs 1203, 1205, and 1207 were filled with buffer only, i.e., no particles. After filling the reservoirs, a electric potential was applied by connecting high voltage source 1214 between reservoir 1201 and the ground electrode 1212. No electric potential was applied to reservoirs 1203, 1205, or 1207. Under these conditions, the particles were transported out of reservoir 1201 toward the ground electrode 1212. The electroosmotic mobility of the bulk fluid was greater than the electrophoretic mobility of the anionic particles. Because the net velocity of the particles, i.e., the electroosmotic velocity of the bulk fluid minus the electrophoretic velocity of the anionic particles, was lower than the electroosmotic velocity, an increase in the average particle velocity was observed as the particles passed from the pumping region 1209 of analysis channel 1208, over the ground electrode 1212, and into the electric field-free region 1210 of analysis channel 1208. Particle velocities were measured before and after the ground electrode using time-lapsed fluorescence CCD imaging, and an electric field strength of 300 V/cm in the pumping region was used. The average particle velocity in the presence of the electric field was 0.7(±0.1)mm/sec(n=21) and in the field free region was 1.9(±0.6)mm/sec(n=7). A velocity increase of 2.6 times was seen as the particles passed over the ground electrode 1212 indicating termination of the electric field by the ground electrode. The electroosmotic mobility generated in the pumping region was estimated to be $6 \times 10^{-4}$ cm$^2$/(V·s) and corresponds to typical electroosmotic mobilities for native glass surfaces. Field strengths greater than 500 V/cm were successfully applied without macroscopic bubble generation.

The bridging membrane embodiment described above suggests a simplistic method for manufacturing fluidic microchips. The fluidic channels are molded as described above or embossed into a planar substrate using an embossing tool that contains the microfluidic channel design. After fabrication of the fluidic substrate a cover plate is formed from a gas porous material similar to that described above. In addition, the electrical contacts are formed on this coverplate material using metal deposition techniques to spatially pattern electrode structures in a desired layout. Other conducting materials besides metals could be used, e.g., conducting polymers, and different deposition or patterning methods could be used such as electrochemical deposition or silk screen patterning. The substrate and coverplate with electrodes are then bonded together using any of a number of approaches including adhesive bonding, covalent bonding, noncovalent bonding, or thermal bonding. The electrode layout provides electrical contact within channels and reservoirs as necessary in addition to electrical contact with the controlling power supply unit that drives the electrokinetic fluid manipulations. In addition the substrate or coverplate could have fluid reservoirs therein. This method of microchip fabrication could be extremely rapid and inexpensive.

Figure 13:
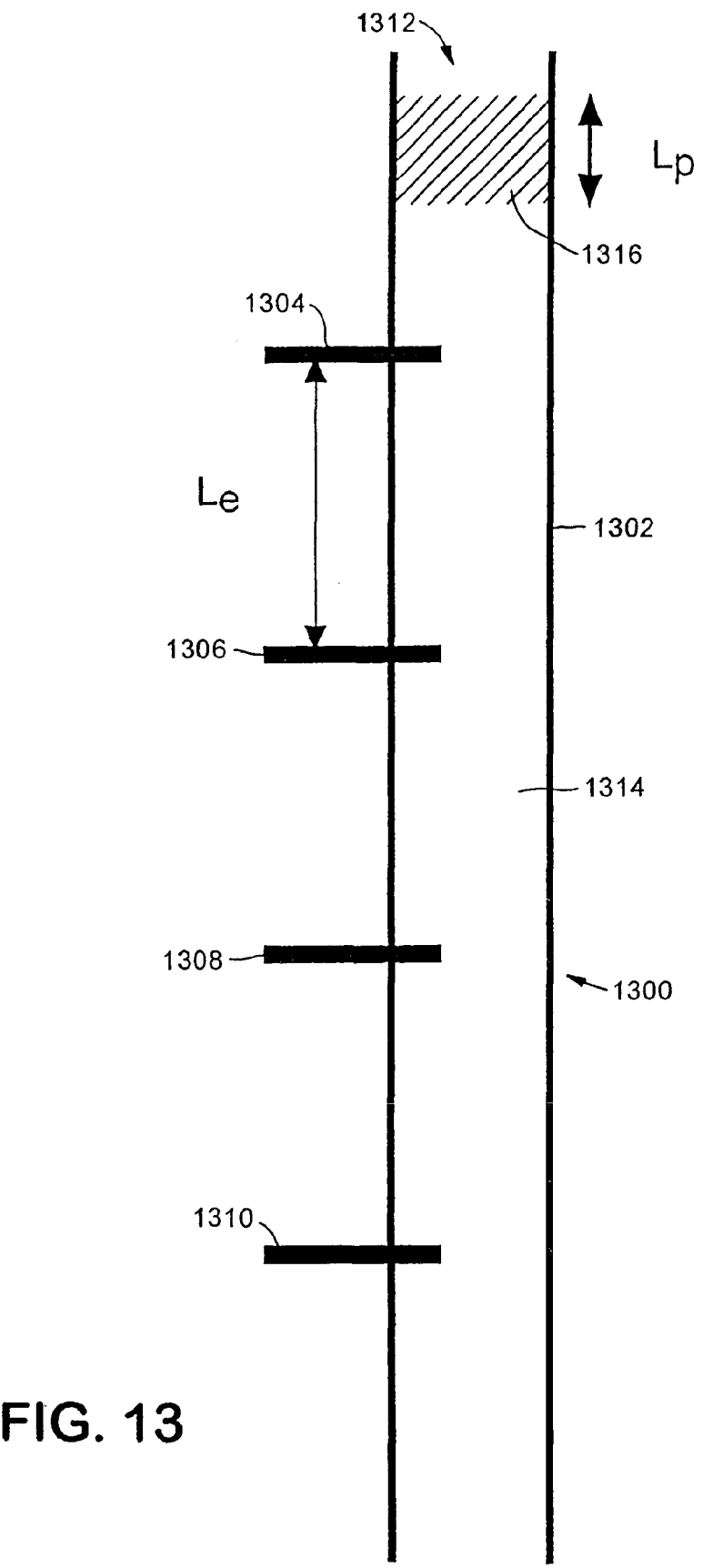
FIG. 13 is a schematic diagram of a microchannel according to another aspect of this invention having a series of bridging membranes for linearly transporting a material along the microchannel.

Shown schematically in FIG. 13 is another application of bridging membranes described above in a microchannel device according to this invention. The device 1300 has a substantially linear microchannel 1302 that has electrical contacts 1304, 1306, 1308, and 1310 disposed at spaced-apart locations along microchannel 1302. The distance $L_e$ between the electrical contacts is preferably fixed so that the contacts are equally spaced. However, it is not necessary to have equally spaced contacts, although such an arrangement is believed to be the most efficient design. The electrical contacts 1304, 1306, 1308, and 1310 are formed of a bridging membrane as described hereinabove with reference to FIG. 1. Alternatively, the electrical contacts can be made using the gas permeable membrane (PDMS) and metal electrode combination described above with reference to FIG. 12. The inlet 1312 of microchannel 1302 is adapted to access at least two different materials. Microchannel 1302 is predominantly filled with a first material 1314 that provides significant electroosmotic mobility. In operation, an electric potential is applied between electrodes 1304 and 1306 to induce electrokinetic transport of the first material toward electrode 1306. In that stage, electrodes 1308 and 1310 are left electrically floating. The inlet 1312 of microchannel 1302 is then brought into communication with a second material for a period of time to generate a plug of the second material 1316 that has an axial extent $L_p$. In the preferred use of device 1300, the second material is nonconducting or does not support electrokinetic transport. In the nonconducting case, the current through electrodes 1304 and 1306 is monitored so as to detect the arrival of the plug 1316 of the second material at electrode 1304. When a current drop is observed, an electric potential is applied between electrodes 1306 and 1308, leaving the others electrically floating. The electrokinetic force to transport material is now induced in microchannel 1302 between electrodes 1306 and 1308. The current through electrodes 1306 and 1308 is monitored. Upon arrival of the plug 1316 of the second material at electrode 1306 a reduction in current is detected at electrode 1306, and the voltage is applied between electrodes 1308 and 1310, while leaving the other electrodes floating. Again, when the plug 1316 of second material arrives at electrode 1308, a current drop occurs through that electrode. That signal resets the device so that the electrical potential is applied between electrodes 1304 and 1306, as in the initial state of operation. The maximum length of the plug 1316 of the second material is given by the following equation.

$$L_p < (n-3)L_e$$

or for n=4, $L_p < L_e$. The minimum distance permitted between two separate plugs of the second material is $2L_e + L_p$. Device 1300 acts as a linear motor that is able to transport either a conducting or nonconducting material along microchannel 1302 by time dependent control of the electrical potentials applied to the series of electrical contacts 1304, 1306, 1308, and 1310.

Another application of a microfluidic device in accordance with this invention uses a plurality of bridging membrane contacts or electrodes as a pump for nonconducting liquids or gases. Such a pump uses a suitable electroosmotic liquid as a working fluid that would cycle repeatedly within the device with little if any loss. The combination of surface tension, vapor pressure, and electroosmotic forces is selected to be sufficient to withstand the pressure at the interface between the working fluid and the gas or liquid being evacuated. The maximum pumping pressure is attained when the electroosmotic flow is counterbalanced by the Poiseuille flow generated by the pressure drop, and depends on the axial electric field and the cross sections of the microchannels used. The vapor pressure of the working fluid is the ultimate limit of the vacuum that can be obtained with such a device. An embodiment of a cyclical pump utilizing this concept is described below.

FIGS. 14A to 14E are schematic diagrams of a two-cycle pump 1400 that is used as a vacuum pump in accordance with this aspect of the invention. The pump 1400 has an inlet 1401 that is connected to a chamber (not shown) to be evacuated. Pump 1400 includes an exhaust port 1402 that is open to the atmosphere and two channels 1404 and 1406 leading from the inlet port 1401 to the exhaust port 1402. Three electrodes 1408a, 1408b, and 1408c, preferably configured as bridging membranes, are disposed at several locations along channel 1404. Another electrode 1408d of similar construction is disposed at a preselected location on channel 1406. There is an additional electrical contact 1409 at the exhaust port 1402 that can be either a bridging membrane or another type of connection, such as a wire inserted in the exhaust opening. Electrical potentials V1, V2, V3, V4, and V5 are selectively applied to the electrodes 1408a, 1408b, 1408c, 1408d, and 1409, respectively, during the operation of the pump 1400. The following operating conditions are selected to provide the desired functionality. First, the voltage difference V4−V5 between the electrical contact 1409 and electrode 1408d and the voltage difference V1−V2 across the electrodes 1408a and 1408b are selected to produce axial electric fields in their respective channels that are sufficiently large to produce an electroosmotic pressure greater than the pressure difference between the exhaust port 1402 and inlet port 1401. The first condition (channel 1406) prevents the working fluid from entering the vacuum chamber during the exhaust stroke while the second condition (channel 1404) ensures that the working fluid can be displaced from the low pressure inlet to the high pressure exhaust. As a third condition, the net electroosmotic pressure produced by the voltage difference between electrodes 1408c and 1408b (V3−V2), between electrodes 1408a and 1408b (V1−V2), and between electrodes 1408c and 1409 (V3−V5) is selected to ensure flow in the counterclockwise direction during the exhaust stroke. The electric potential applied to electrode 1408c has a value V3 and the value of V3 that meets this third condition is $V3_{high}$. $V3_{high}$ is the value of V3 prior to the start of the intake stroke. The spacing between electrodes and the magnitudes of the applied voltages are selected to meet the above conditions.

Figure 14E:
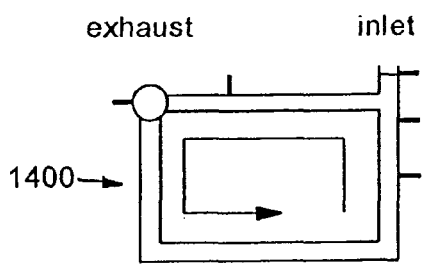
FIGS. 14A-14E are schematic diagrams showing the arrangement and operating sequence of a microfluidic vacuum pump utilizing bridging membranes.
Figure 14D:
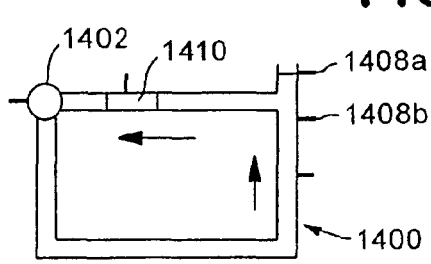
Figure 14A:
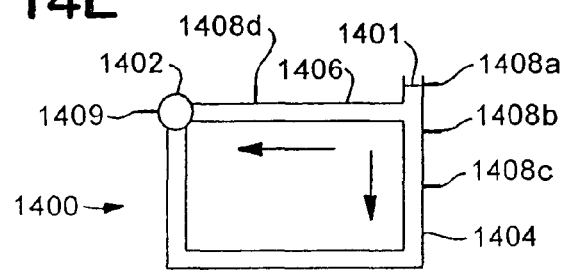
Figure 14C:
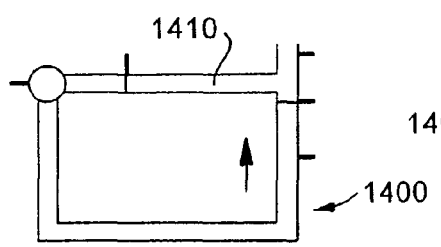
Figure 14B:
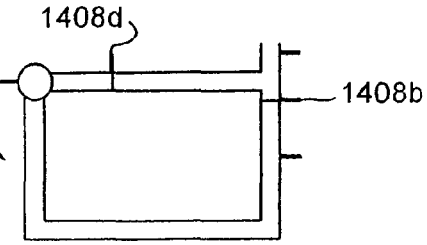

The two strokes of the pumping cycle, intake and exhaust, are obtained by varying the voltage at electrode 1408c as shown in FIGS. 14A-14E. To start the intake stroke, the voltage at electrode 1408c is set equal to that at the exhaust port electrode 1409 as shown in FIG. 14A. The value of V3 at this stage is $V3_{low}$. Under that condition, the working fluid is pumped towards the exhaust port 1402 through both channels 1404 and 1406. The fluid flow stops when the gas-fluid interface in channel 1404 reaches electrode 1408b and the gas-fluid interface in channel 1406 reaches electrode 1408d as shown in FIG. 14B. Flow stops at this point because if the working fluid moved past those electrodes, the electrical conduction path in the channel would be broken and the electrical current driving the flow would be interrupted. At the end of the intake stroke, the portion of channel 1404 between the electrode 1408a and electrode 1408b is filled with gas at the pressure remaining in the vacuum chamber. Similarly, the portion of channel 1406 between the electrode 1408a and electrode 1408*d* is filled with gas at the pressure remaining in the vacuum chamber. The exhaust stroke is started by increasing the voltage at electrode 1408*c* to its initial value, V3$_{high}$, as shown in FIG. 14C. Because of the third condition identified above, the working fluid is electroosmotically pumped in a counterclockwise direction, driven by the voltage difference V3–V2, first filling channel 1404 up to electrode 1408*a*, where the interface is stopped because of the resumption of electrical current conduction between electrodes 1408*a* and 1408*b* as shown in FIG. 14D. The flow then continues towards the exhaust port 1402, pushing out the entrained gas 1410, which is now compressed to the exhaust pressure. Once electrical conduction is re-established between electrodes 1408*d* and 1409, FIG. 14E, the cycle can be repeated.

The pumping device according to this invention is not constrained to operate between vacuum and atmospheric pressure. Any liquid or gas that is immiscible with the working fluid and does not itself undergo electroosmotic flow can be pumped in this way. If the desired pumping speed cannot be attained at a given pressure differential with one channel, as described above, several channels could be connected in parallel between electrodes 1408*a* and 1409 to increase the capacity while maintaining the required pressure differential.

A still further application of a bridging membrane in accordance with another aspect of this invention relates to microfluidic valving. A microchannel network 1500 for implementing this application is shown schematically in FIG. 15. A plurality of microchannels 1501, 1503, 1505, and 1507 are interconnected at a common junction 1520. Reservoirs 1502, 1504, 1506, and 1508 are in fluid communication with the microchannels 1501, 1503, 1505, and 1507, respectively. Bridging membranes 1510, 1512, 1514, and 1516 are disposed at preselected locations along microchannels 1501, 1503, 1505, and 1507 between the reservoirs 1502, 1504, 1506, and 1508, respectively, and the common intersection 1520. Electrical potentials are selectively applied between the reservoirs 1502, 1504, 1506, and 1508 and their corresponding bridging membranes 1510, 1512, 1514, and 1516, respectively, to pump materials from the reservoirs through the fluidic microchannels.

In a first mode of operation, appropriate potentials are applied between reservoirs 1502 and 1508 and bridging membranes 1510 and 1516, respectively, to transport first and second materials from reservoirs 1502 and 1508, respectively, through channels 1501 and 1507 into the common intersection 1520. No potentials need be applied to reservoirs 1504 or 1506 or to bridging membranes 1512 or 1514. The first material is transported from channel 1501 into channel 1503, and the second material is transported from channel 1507 into channels 1503 and 1505. The electrical potential at reservoir 1508 is then removed or lowered relative to the electrical potential at reservoir 1502. This causes the first material to be transported into channel 1505. The electrical potential at reservoir 1508 is then returned to its initial value to terminate the transporting of the first material into channel 1505.

In a second mode of operation, first and second materials are drawn from their respective reservoirs into the common intersection instead of being pushed as in the first mode of operation. Appropriate potentials are applied between reservoirs 1504 and 1506 and bridging membranes 1512 and 1514, respectively, to draw the first and second materials from reservoirs 1502 and 1508, respectively, through channels 1501 and 1507 into the common intersection 1520. No electrical potentials need be applied to reservoirs 1502 and 1508 or to bridging membranes 1510 and 1516. As in the first mode of operation, the first material is transported from channel 1501 into channel 1503, and the second material is transported from channel 1507 into channels 1503 and 1505. The electrical potential at reservoir 1504 is removed or lowered relative to the electrical potential at reservoir 1506 to transport the first material into channel 1505. The electrical potential at reservoir 1503 is then returned to its initial value to terminate the transporting of the first material into channel 1505.

Figure 15:
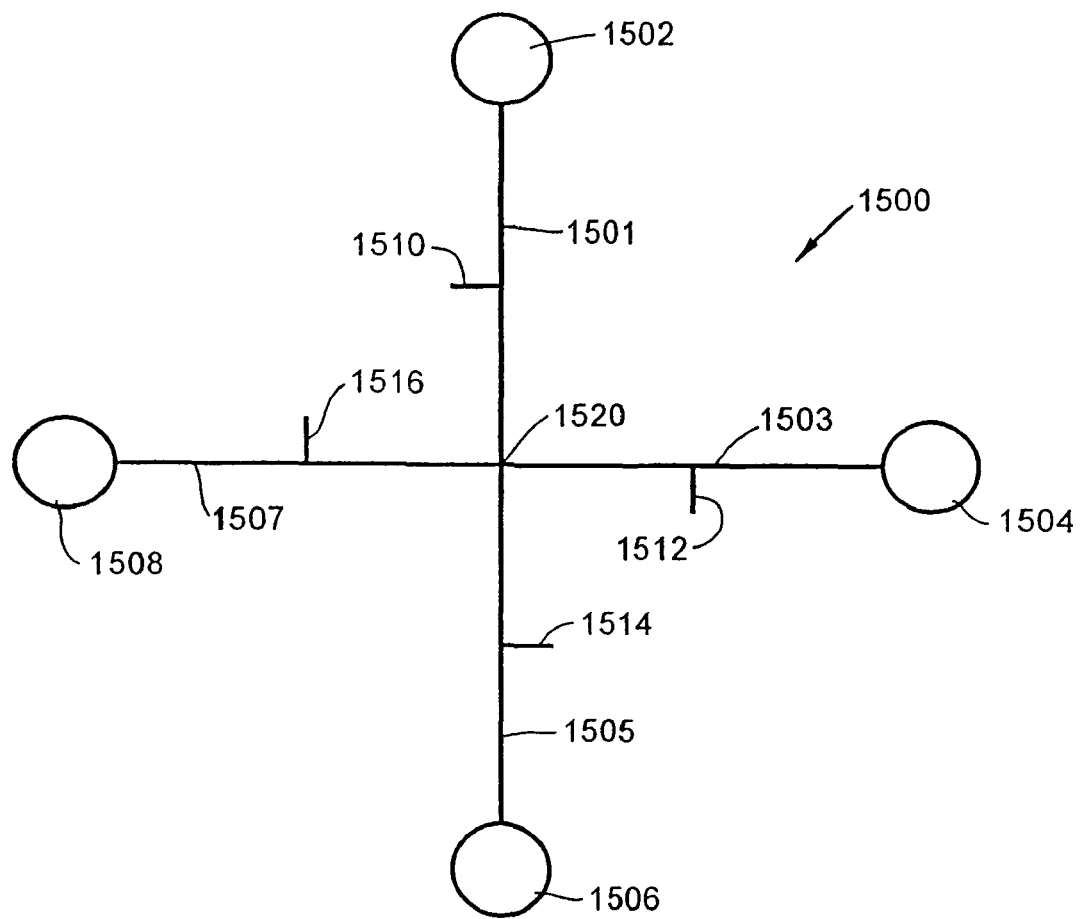
FIG. 15 is a schematic diagram showing a cross arrangement of microchannels and bridging membranes in accordance with a further aspect of this invention for accomplishing microfluidic valving of a fluidic material.

In both the first and second modes of operation of the microchannel network shown in FIG. 15, the electrical potentials at reservoirs 1508 and 1506 can be raised relative to the potentials at reservoirs 1502 and 1504 for the respective material dispensing schemes. Also, bridging membranes 1510 and 1516 or 1512 and 1514 can be connected to a common potential or ground. In the first mode of operation, reservoirs 1504 and 1506 can be combined into a single, common reservoir.

In a third mode of operation, appropriate electrical potentials are applied between reservoirs 1502, 1508, and 1506, and bridging membranes 1510, 1516, and 1514 such that first, second, and fourth materials are transported from reservoirs 1502, 1508, and 1506, respectively, through channels 1501, 1507, and 1505, respectively, into channel 1503. At equilibrium, the proportions of the first, second, and fourth materials in the common intersection 1520 are constant. In a variation of this mode of operation, the transporting of the first, second, and fourth materials can be accomplished by applying an appropriate electrical potential between reservoir 1504 and bridging membrane 1512, and having the channels 1501, 1503, 1505, and 1507 dimensioned appropriately. The second material is dispensed into channel 1505 by applying appropriate potentials between reservoirs 1508, 1504, and 1506 and bridging membranes 1516, 1512, and 1514, respectively. The dispensing of the second material into channel 1505 can be accomplished by applying an appropriate electrical potential between reservoir 1502 and bridging membrane 1510, and having channels 1501, 1503, 1505, and 1507 dimensioned appropriately. In addition, bridging membranes 1510, 1512, 1514, and 1516 can be connected to a common potential or to ground.

In any of the modes of operation described for the microchannel network 1500 shown in FIG. 15, the electrical potentials can be applied between any combination of reservoirs and corresponding bridging membranes to enhance or diminish the transport of material within the respective channel or channels.

Figure 16:
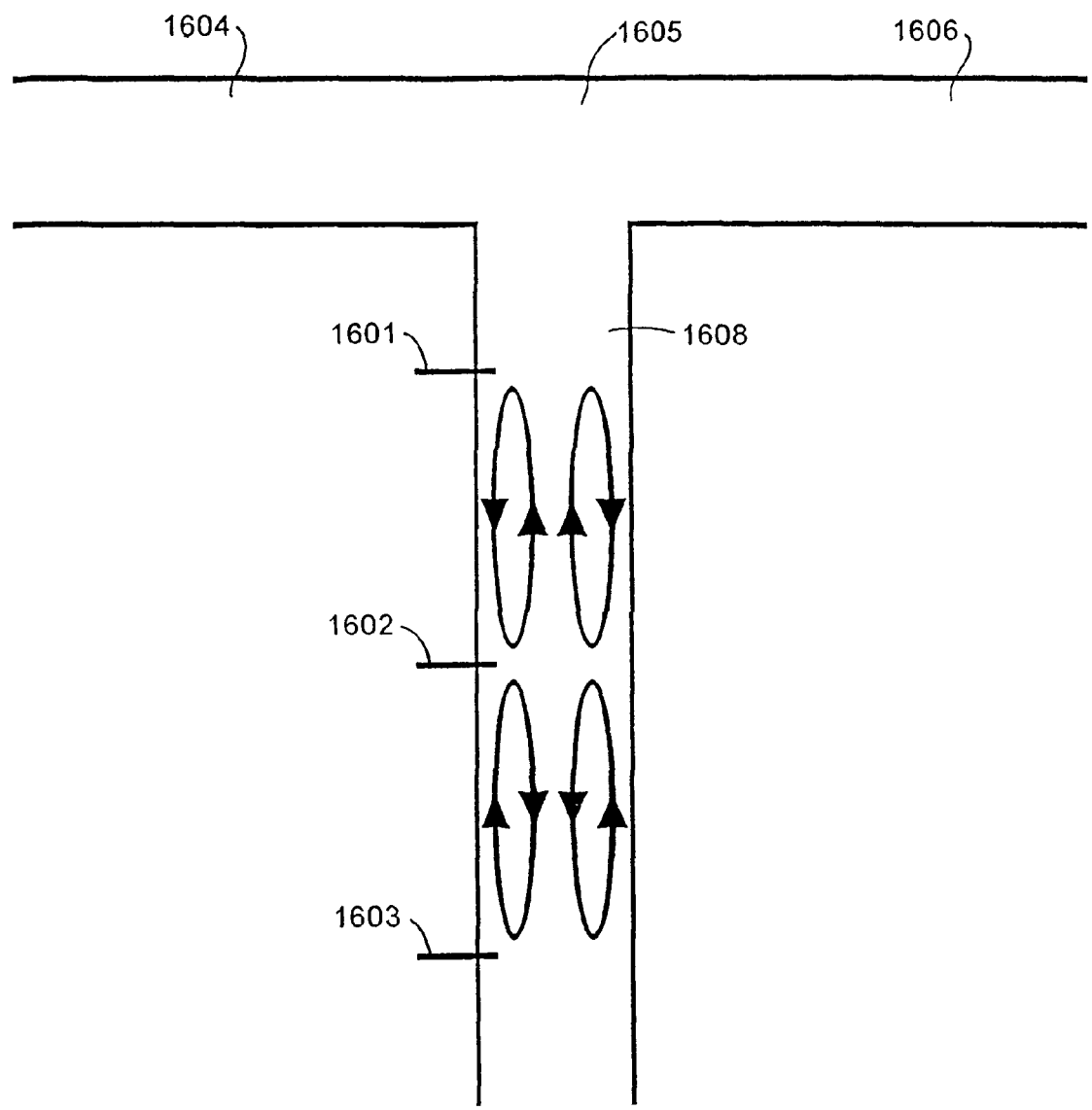
FIG. 16 is a schematic diagram of an arrangement of microchannels and bridging membranes in accordance with another aspect of this invention for mixing of fluidic materials.

Yet another microchannel arrangement employing bridging membranes in accordance with this invention is shown in FIG. 16. In this implementation a group of three bridging membranes 1601, 1602, and 1603 is used to provide mixing of materials that are supplied from a mixing tee 1605. A first material is supplied from microchannel 1604 and a different material is supplied from microchannel 1606. The first and second materials are electrokinetically transported through tee intersection 1605 into the mixing microchannel 1608 by applying appropriate voltages to channels 1604 and 1606 relative to channel 1608. The bridging membranes 1601, 1602, and 1603 are attached to channel 1608 so as to form three spatially distinct electrical contacts or electrodes. Voltages are applied to bridging membranes 1601 and 1603 relative to bridging membrane 1602 for generating opposing electrokinetic forces on the fluid which cause circulation patterns in the transported materials similar to those indicated by the arrows in FIG. 16. In practice, the fluid motion is three-dimensional with the flow near the channel walls being toward bridging membrane 1602 and the flow in the center of the channel being away from bridging membrane 1602. Materials are mixed in this fashion under either stopped flow or continuous flow conditions, i.e., the average net velocity of the materials in the channel 1608 being zero or non-zero, respectively. A series of such mixers could also be cascaded for enhanced mixing of the materials.

Several embodiments of a microfabricated device in accordance with the present invention have been described hereinabove. The microfabricated devices which utilize a bridging membrane overcome many of the limitations of the known devices. Devices constructed in accordance with the concepts of this invention permit several advantageous modes of operation. More particularly, an embodiment has been described that provides sample loading and injection with a minimum of electrochemically generated byproducts. Another embodiment of the present invention has been described that enables the transport of fluidic materials by electroosmotic forces in a channel region that is uninfluenced by an electric field. A further embodiment has been described that provides the ability to concentrate ionic species in an analysis channel. Still other embodiments of the present invention have been described which facilitate the separation or purification of sample material, that facilitate the removal of electrochemically generated gas species from the sample and transport materials, that provide either positive or negative pressure to facilitate hydraulic transport of fluidic materials, and that provide valving of fluidic materials in a microfluidic structure.

The terms and expressions which have been employed are used as terms of description and not of limitation. There is no intention in the use of such terms and expressions of excluding any equivalents of the features shown and described or portions thereof. It is recognized, however, that various modifications such as channel dimension, location, and arrangement are possible within the scope of the invention as claimed.

What is claimed is:

1. A device for the manipulation of liquid phase materials, comprising:
    a substrate;
    a channel disposed in said substrate and containing a material, said channel having first and second ends;
    an electrode made of an electrically conducting material, said electrode being in electrical contact with said channel at a location along said channel that is intermediate the first and second ends thereof;
    a coverplate;
    said coverplate and said substrate being mated together such that the coverplate seals the channel wherein either said substrate or said coverplate is formed of a gas permeable material that is selected to facilitate the removal of electrochemically generated gases from said channel; and
    means for applying an electric potential in a first segment of the channel between the first end of said channel and said electrode such that an electric field-free region is created in a second segment of said channel between said electrode and the second end, whereby transport of the material can be induced in the first and second segments of the channel.

2. A device as set forth in claim 1 wherein the coverplate is made of the gas permeable material and the electrode is formed on the substrate.

3. A device as set forth in claim 1 wherein the substrate is made of the gas permeable material and the electrode is formed on the substrate.

4. A device as set forth in claim 1 wherein the substrate is made of the gas permeable material and the electrode is formed on the coverplate.

5. A device as set forth in claim 1 wherein the cover plate is made of the gas permeable material and the electrode is formed on the coverplate.

6. A device as set forth in claim 1 wherein both the substrate and the coverplate are formed of the gas permeable material.

7. A method for the manipulation of liquid phase materials, comprising the steps of:
    providing a microchannel device that includes a substrate having a channel formed therein, an electrode made of an electrically conducting material, said electrode being in electrical contact with said channel at a location along said channel that is intermediate first and second ends thereof, and a coverplate for sealing the channel, wherein either said substrate or said coverplate is formed of a gas permeable material that is selected to facilitate the removal of electrochemically generated gases from said channel;
    providing a material in the channel; and
    inducing transport of the material in a first segment of said channel between said electrode and the first end of said channel and creating an electric field-free region in a second segment of said channel between the electrode and the second end of said channel by applying an electric potential between the first end of said channel and said electrode, whereby the material is transported in the first and second segments of said channel.

8. A method for the manipulation of liquid phase materials, comprising the steps of:
    providing a microchannel device that includes a substrate having a channel formed therein, first and second electrodes made of an electrically conducting material, said electrodes being in electrical contact with said channel at spaced apart locations along said channel that are intermediate first and second ends thereof, and a coverplate for sealing the channel, wherein either said substrate or said coverplate is formed of a gas permeable material that is selected to facilitate the removal of electrochemically generated gases from said channel;
    providing a material in the channel; and
    inducing transport of the material in a first segment of said channel by applying an electric potential between said first and second electrodes and creating electric field-free regions in a second segment of said channel between said first electrode and the first end of said channel and in a third segment of said channel between the second electrode and the second end of said channel, whereby the material is transported in the first, second, and third segments.

9. A method as set forth in claim 7 or 8 wherein both the substrate and the coverplate are formed of the gas permeable material.

10. A method as set forth in claim 7 or 8 wherein the step of inducing transport of the material in the channel comprises the step of applying the electric potential with a polarity such that transport of the material proceeds in a direction from the first end of the channel toward the second end of the channel.

11. A method as set forth in claim 7 or 8 wherein the step of inducing transport of the material in the channel comprises the step of applying the electric potential with a polarity such that transport of the material proceeds in a direction from the second end of the channel toward the first end of the channel.

12. A device for the manipulation of liquid phase materials, comprising:
    a substrate;
    a channel disposed in said substrate and containing a first material, said channel having first and second ends;

first and second electrodes each made of an electrically conducting material, said electrodes being in electrical contact with said channel at spaced apart locations along said channel that are intermediate the first and second ends thereof;

a coverplate;

said coverplate and said substrate being mated together such that the coverplate seals the channel, said substrate or said coverplate being formed of a gas permeable material that is selected to facilitate the removal of electrochemically generated gases from said channel; and means for applying an electric potential in a first segment of the channel between the first and second electrodes such that electric field-free regions are created in a second segment of the channel between the first end of the channel and the first electrode and in a third segment of the channel between the second electrode and the second end of the channel, whereby transport of the first material can be induced in the first segment of the channel, in the second segment of said channel, and in the third segment of said first channel.

13. A device as set forth in claim 12 wherein both the substrate and the coverplate are formed of the gas permeable material.

* * * * *